US009182330B2

(12) United States Patent
Kismarton et al.

(10) Patent No.: US 9,182,330 B2
(45) Date of Patent: Nov. 10, 2015

(54) APPARATUS, SYSTEM AND METHOD FOR COMPRESSION TESTING OF TEST SPECIMENS

(71) Applicant: The Boeing Company, Chicago, IL (US)

(72) Inventors: Max U. Kismarton, Renton, WA (US); Kenneth H. Griess, Kent, WA (US)

(73) Assignee: The Boeing Company, Chicago, IL (US)

( * ) Notice: Subject to any disclaimer, the term of this patent is extended or adjusted under 35 U.S.C. 154(b) by 292 days.

(21) Appl. No.: 13/947,050

(22) Filed: Jul. 20, 2013

(65) Prior Publication Data

US 2015/0020603 A1    Jan. 22, 2015

(51) Int. Cl.
*G01N 3/02* (2006.01)
*G01M 5/00* (2006.01)
(Continued)

(52) U.S. Cl.
CPC .............. *G01N 3/02* (2013.01); *G01M 5/005* (2013.01); *G01M 5/0091* (2013.01); *G01M 11/081* (2013.01); *G01N 3/04* (2013.01); *G01N 3/08* (2013.01); *G01N 2203/0003* (2013.01); *G01N 2203/0019* (2013.01); *G01N 2203/027* (2013.01); *G01N 2203/0282* (2013.01);
(Continued)

(58) Field of Classification Search
CPC ............. G01N 3/02; G01N 3/04; G01N 3/08; G01N 2203/0282; G01N 2203/0019; G01N 2203/0003; G01N 2203/0641; G01N 2203/0027; G01N 2203/0447; G01M 5/005; G01M 11/08
USPC .................... 73/818, 821, 825, 774, 800, 802
See application file for complete search history.

(56) References Cited

U.S. PATENT DOCUMENTS 3,559,473 A    2/1971    Dudderar et al.
3,795,134 A    3/1974    Eichenbrenner et al.
(Continued)

FOREIGN PATENT DOCUMENTS

FR    2695207 A1    3/1994
GB    2011096 A    7/1979

OTHER PUBLICATIONS

Extended European Search Report mailed Nov. 27, 2014, for counterpart EP application EP14176276.5-1553, Applicant The Boeing Company, 10 pages.
(Continued)

*Primary Examiner* — Lisa Caputo
*Assistant Examiner* — Jonathan Dunlap

(57) ABSTRACT

There is provided an apparatus for compression testing. The apparatus has a base assembly having an end load element attached to the base assembly, the base assembly being rigid. The apparatus has a support assembly attached to the base assembly, and having a plurality of window portions. The apparatus has a core assembly installed within the support assembly, the core assembly being crushable and configured to protect the support assembly and the base assembly from fracture loads generated during compression testing. The base assembly, the support assembly, and the core assembly together form an apparatus for compression testing of a test specimen having a notch portion. The apparatus is configured for use with an optical strain measurement system. When the test specimen is installed in the support assembly, the test specimen and the notch portion are visible to the optical strain measurement system through the plurality of window portions.

20 Claims, 19 Drawing Sheets

(51) Int. Cl.
*G01N 3/04* (2006.01)
*G01N 3/08* (2006.01)
*G01M 11/08* (2006.01)

(52) U.S. Cl.
CPC *G01N2203/0447* (2013.01); *G01N 2203/0641* (2013.01)

(56) References Cited

U.S. PATENT DOCUMENTS 5,297,441 A 3/1994 Smith et al.
6,952,969 B2 * 10/2005 O'Brien et al. ................. 73/818

OTHER PUBLICATIONS

Sanchez-Saez, S. et al., "Compression after impact of thin composite laminates", Composites Science and Technology, Elsevier, UK, vol. 65, No. 13, Jun. 8, 2005, pp. 1911-1919, XP027688145, ISSN: 0266-3538 (abstract; figures 1, 4, 5).

Feraboli, Paolo, "Development of a Modified Flat-plate Test Specimen and Fixture for Composite Materials Crush Energy Absorption", Dpt. of Aeronautics and Astronautics, Univ. of Washington, Seattle, WA, Journal of Composite Materials, vol. 43, No. 19, Jul. 20, 2009, pp. 1967-1990, XP055153401, DOI: 10.1177/0021998309343025 (abstract; figures 8-10).

Web pages from GOM website at web address <http://www.gom.com>, regarding information for ARAMIS Optical 3D Deformation Analysis system and device, as of Apr. 6, 2013, 7 pages.

* cited by examiner

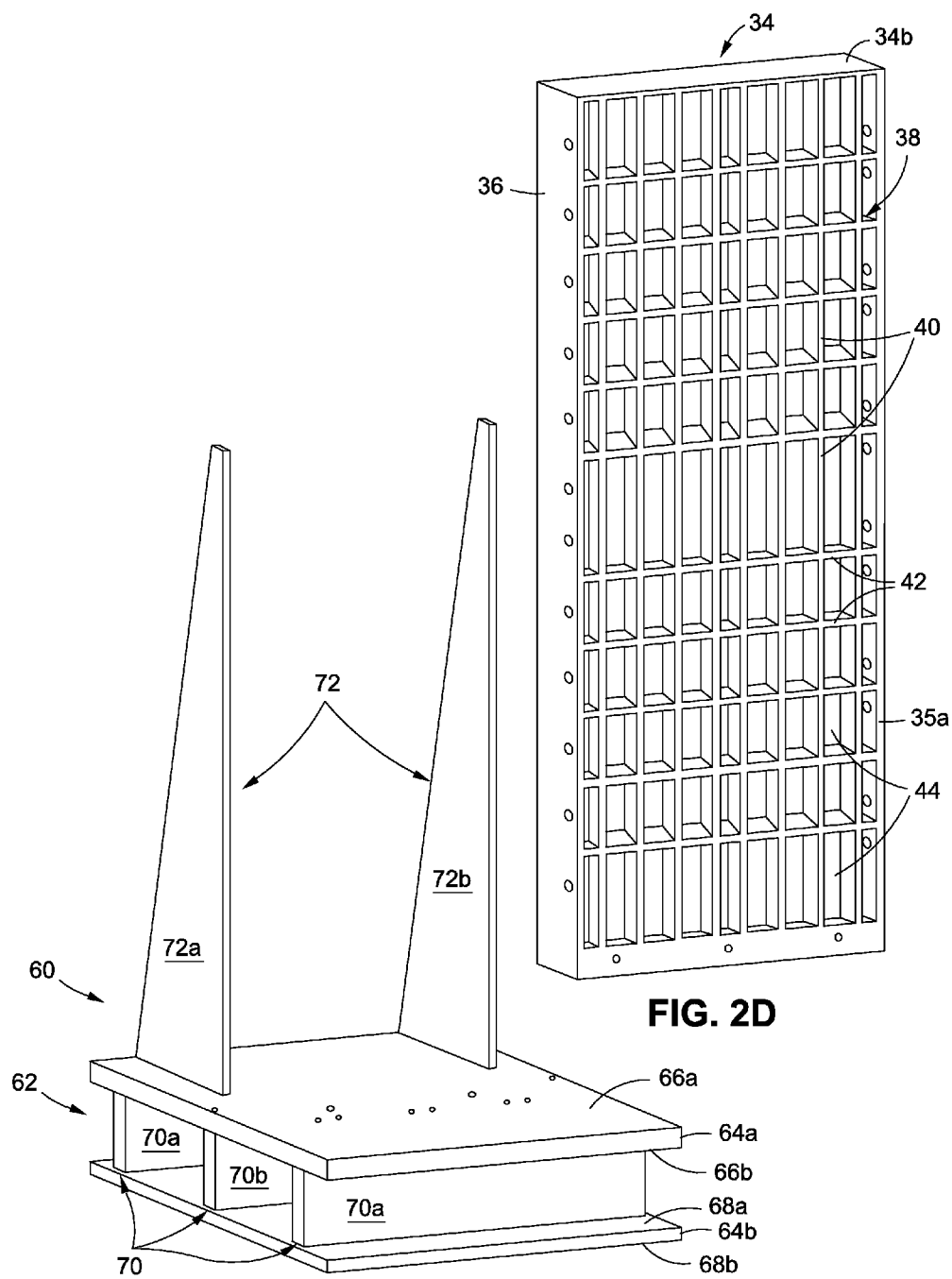

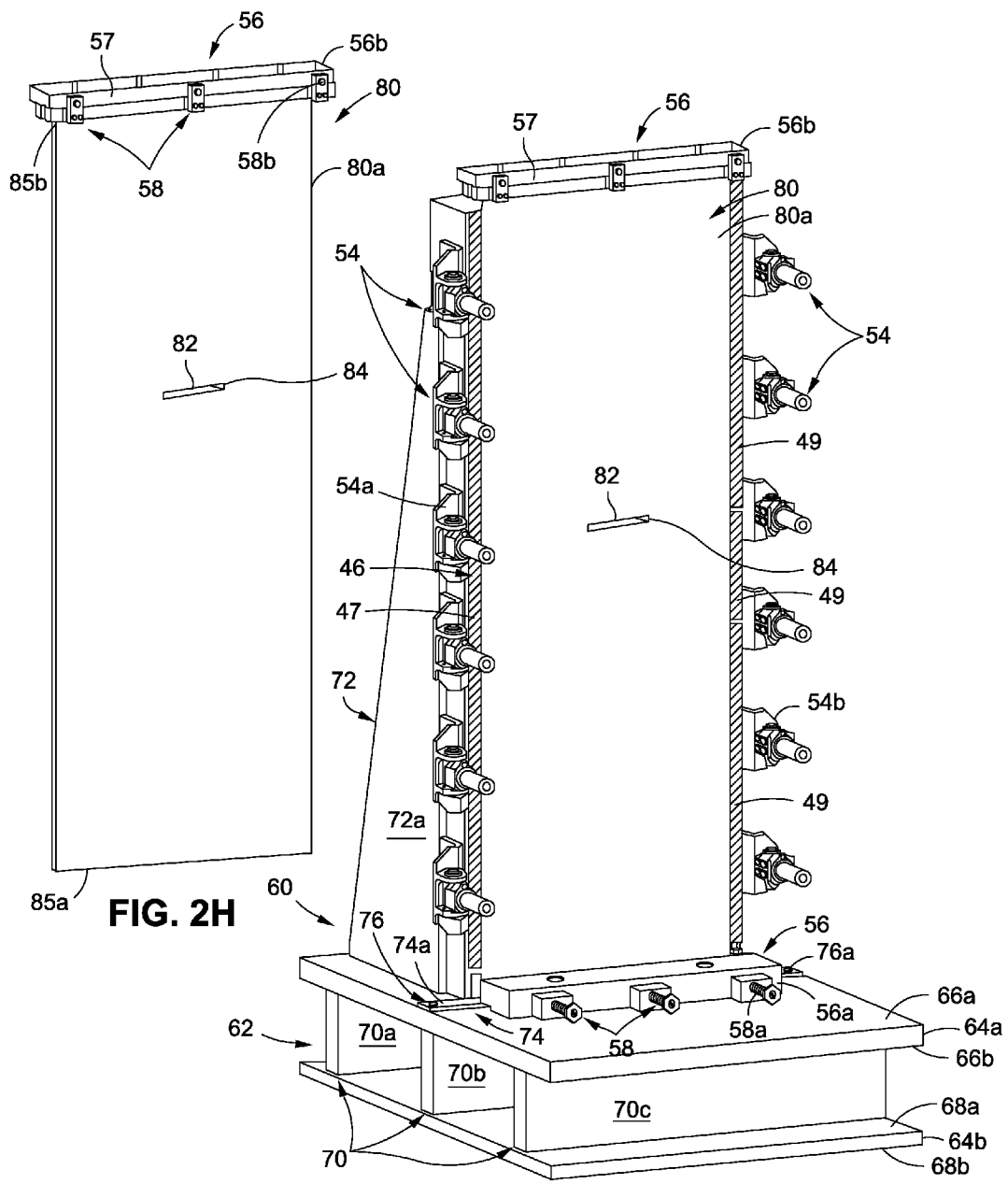

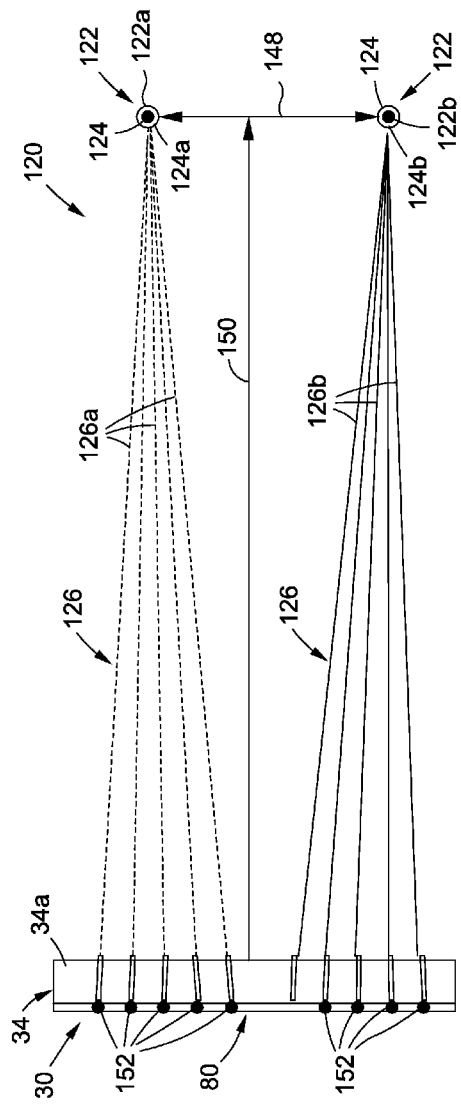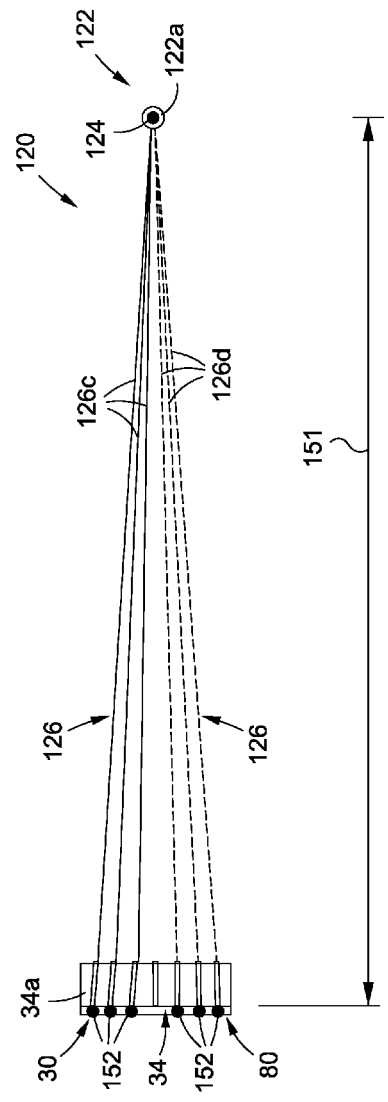

APPARATUS, SYSTEM AND METHOD FOR COMPRESSION TESTING OF TEST SPECIMENS

BACKGROUND

1) Field of the Disclosure

The disclosure relates generally to apparatus assemblies, systems and methods for compression testing of test specimens, and more particularly, to apparatus assemblies, systems and methods for compression testing of large notch compression test panels, such as panels of component parts of air vehicles.

2) Description of Related Art

Mechanical testing of component parts, or of test specimens of component parts, is often performed in the manufacture of air vehicles, such as aircraft, rotorcraft, spacecraft, and other air vehicles. Mechanical testing provides material property data, such as strength, hardness ductility, and other data about the material as tested under various conditions, such as compression, tension, load and temperature. In turn, the mechanical testing provides information relating to the suitability of a material for its intended application. Such information aids in the design of component parts that will perform as expected.

Mechanical testing of component parts of air vehicles may include compression testing. Compression testing determines the behavior of materials, such as composite or metal materials, under compressive load conditions. Compression testing may be conducted by loading a test specimen, such as a test panel or a flat piece of laminate referred to as a "coupon", between two support plates of a test fixture.

The test fixture is typically installed in a testing machine, for example, a universal testing machine. The testing machine may apply a compression force or load to the test specimen and may compress the test specimen in a lengthwise direction until it fractures or breaks. The testing machine may record the force required to fracture or break the test specimen. Compressive strength of the test specimen material may be measured by plotting applied force or load versus deformation of the test specimen material. As used herein, "compressive strength" means the maximum compressive load or stress the test specimen material is capable of withstanding before fracturing or breaking.

Test fixtures, apparatus assemblies, and methods for compression testing of air vehicle component parts exist. For example, FIG. 1 is an illustration of a front perspective view of an existing test fixture 10 for compression testing, such as in the form of an existing large notch compression (LNC) test fixture 10a. As shown in FIG. 1, the existing test fixture 10 has a first support plate 12a and a second support plate 12b that sandwich a test specimen panel 28 therebetween. The test specimen panel 28 may be in the form of a large notch compression (LNC) panel.

As further shown in FIG. 1, the first support plate 12a and the second support plate 12b of the existing test fixture 10 completely cover the test specimen panel 28 and obstruct any view of the test specimen panel 28. Thus, use of such existing test fixture 10 precludes use with existing optical strain measurement systems that may be used to optically obtain information relating to strain measurements of the test specimen panel 28.

Instead of using existing optical strain measurement systems, the existing test fixture 10 requires the use of a plurality of strain gages 14 (see FIG. 1) to measure the strain of the test specimen panel 28. As shown in FIG. 1, each strain gage 14 may be positioned laterally across the first support plate 12a, and each strain gage 14 may be coupled to hinge attachment elements 16 mounted on a frame portion 18 of the existing test fixture 10.

However, the use of such strain gages 14 (see FIG. 1) may involve extensive installation time and labor, which results in increased flow time. In addition, the use of such strain gages 14 (see FIG. 1) may require precise alignment and calibration operations, as well as connection to a strain gage machine, prior to testing. This may, in turn, result in increased time and expense of testing. Due to the extensive time involved in installing the strain gages 14 (see FIG. 1) on the existing test fixture 10 (see FIG. 1), test specimen panels 28 may only be tested at a test rate of one (1) or two (2) test specimen panels 28 per day.

As further shown in FIG. 1, the existing test fixture 10 has a base portion 22 and a side support portion 24 (one on each side). However, the base portion 22 may be thin and wear out after several compression tests. Shimming may be required to reinforce the base portion 22 and to hold the first support plate 12a, the second support plate 12b, and the test specimen panel 28 in place. For example, shims 20 (see FIG. 1) may be installed on the existing test fixture 10 (see FIG. 1). However, such shimming process may involve extensive installation time and labor prior to testing. This may, in turn, result in increased time and expense of testing.

Thus, existing methods for compression testing of test specimen panels, such as large notch compression panels, may be expensive and may take four (4) to ten (10) weeks or more to complete. Accordingly, there is a need in the art for an improved apparatus, system and method for compression testing of test specimens, such as large notch compression test panels of component parts of air vehicles, that provide advantages over known apparatus assemblies, systems and methods.

SUMMARY

This need for an improved apparatus, system and method for compression testing of test specimens, such as large notch compression test panels of component parts of air vehicles is satisfied by this disclosure. As discussed in the below detailed description, embodiments of the improved apparatus, system and method for compression testing of test specimens, such as large notch compression test panels of component parts of air vehicles, may provide significant advantages over known apparatus assemblies, systems and methods.

In one embodiment of the disclosure, there is provided an apparatus for compression testing. The apparatus comprises a base assembly having an end load element attached to the base assembly, the base assembly being rigid. The apparatus further comprises a support assembly attached to the base assembly, the support assembly having a plurality of window portions. The apparatus further comprises a core assembly installed within the support assembly, the core assembly being crushable and configured to protect the support assembly and the base assembly from fracture loads generated during compression testing.

The base assembly, the support assembly, and the core assembly together comprise an apparatus for compression testing of a test specimen having a notch portion. The apparatus is configured for use with an optical strain measurement system. When the test specimen is installed in the support assembly, the test specimen and the notch portion are visible to the optical strain measurement system through the plurality of window portions.

In another embodiment of the disclosure, there is provided a system for compression testing. The system comprises an apparatus for compression testing. The apparatus comprises a base assembly having an end load element attached to the base assembly, the base assembly being rigid. The apparatus further comprises a support assembly attached to the base assembly, the support assembly having a plurality of window portions. The apparatus further comprises a core assembly installed within the support assembly, the core assembly being crushable and configured to protect the support assembly and the base assembly from fracture loads generated during compression testing.

The system further comprises a test specimen having a notch portion. The test specimen is installed in the support assembly of the apparatus. The system further comprises a testing machine configured to apply one or more compression loads to the test specimen when the apparatus with the test specimen is installed in the testing machine. The system further comprises a testing machine controller coupled to the testing machine and configured to control operation of the testing machine.

The system further comprises an optical strain measurement system positioned in relation to the apparatus with the test specimen installed in the testing machine, so that the test specimen and the notch portion are visible to the optical strain measurement system through the plurality of window portions. The system further comprises a data acquisition system coupled to the optical strain measurement system. The apparatus, the test specimen, the testing machine, the testing machine controller, the optical strain measurement system, and the data acquisition system together comprise a system for compression testing of the test specimen.

In another embodiment of the disclosure, there is provided a method for compression testing. The method comprises the step of forming an apparatus for compression testing of a test specimen. The apparatus comprises a base assembly having an end load element attached to the base assembly, the base assembly being rigid. The apparatus further comprises a support assembly attached to the base assembly, the support assembly having a plurality of window portions. The apparatus further comprises a core assembly installed within the support assembly, the core assembly being crushable and configured to protect the support assembly and the base assembly from fracture loads generated during compression testing.

The method further comprises the step of forming a notch portion in a test specimen. The method further comprises the step of installing the test specimen within the support assembly and adjacent to the core assembly. The method further comprises the step of installing the apparatus in a testing machine for compression testing.

The method further comprises the step of positioning an optical strain measurement system in relation to the apparatus, so that the test specimen and the notch portion are visible to the optical strain measurement system through the plurality of window portions. The method further comprises the step of applying one or more compression loads to the test specimen. The method further comprises the step of measuring strain data of the test specimen with the optical strain measurement system.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein:

FIG. 2C is an illustration of a front perspective view of a base assembly of the apparatus of FIG. 2A;

FIG. 2D is an illustration of a front perspective view of a support grid of the apparatus of FIG. 2A;

FIG. 2H is an illustration of a front perspective view of a test specimen used in the apparatus of FIG. 2A;

FIG. 2I is an illustration of a front perspective view of the test specimen of FIG. 2H installed in front of the core assembly and on the base assembly of FIG. 2E;

FIG. 4A is an illustration of a side view of an exemplary embodiment of an optical strain measurement system that may be used in the system of FIG. 3A, showing the optical strain measurement system positioned in front of the apparatus of the disclosure;

FIG. 4B is an illustration of a top view of the optical strain measurement system of FIG. 4A positioned in front of the apparatus of the disclosure;

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and will fully convey the scope of the disclosure to those skilled in the art.

Figure 2A:
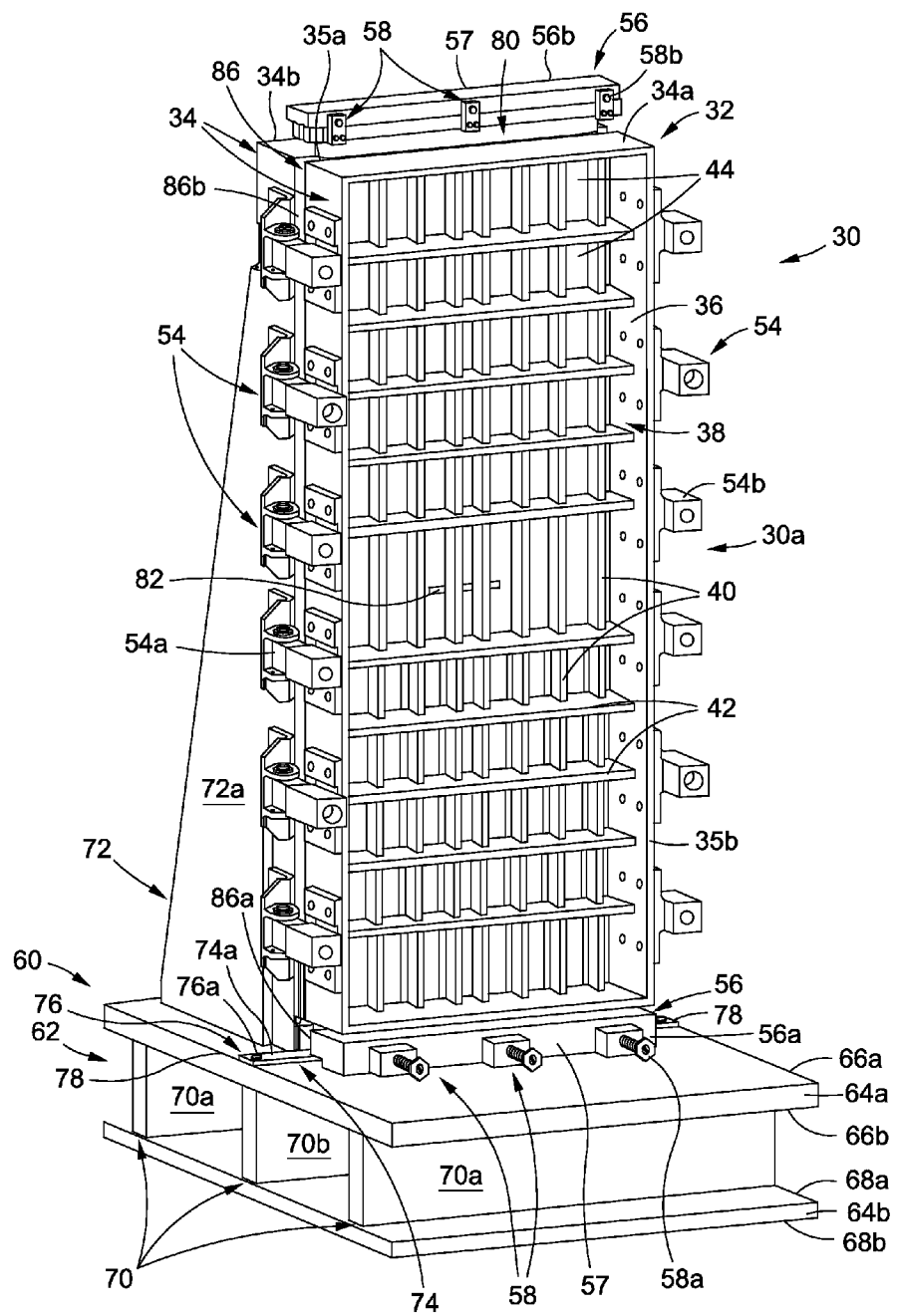
FIG. 2A is an illustration of a front perspective view of an exemplary embodiment of an apparatus for compression testing of the disclosure.
Figure 2B:
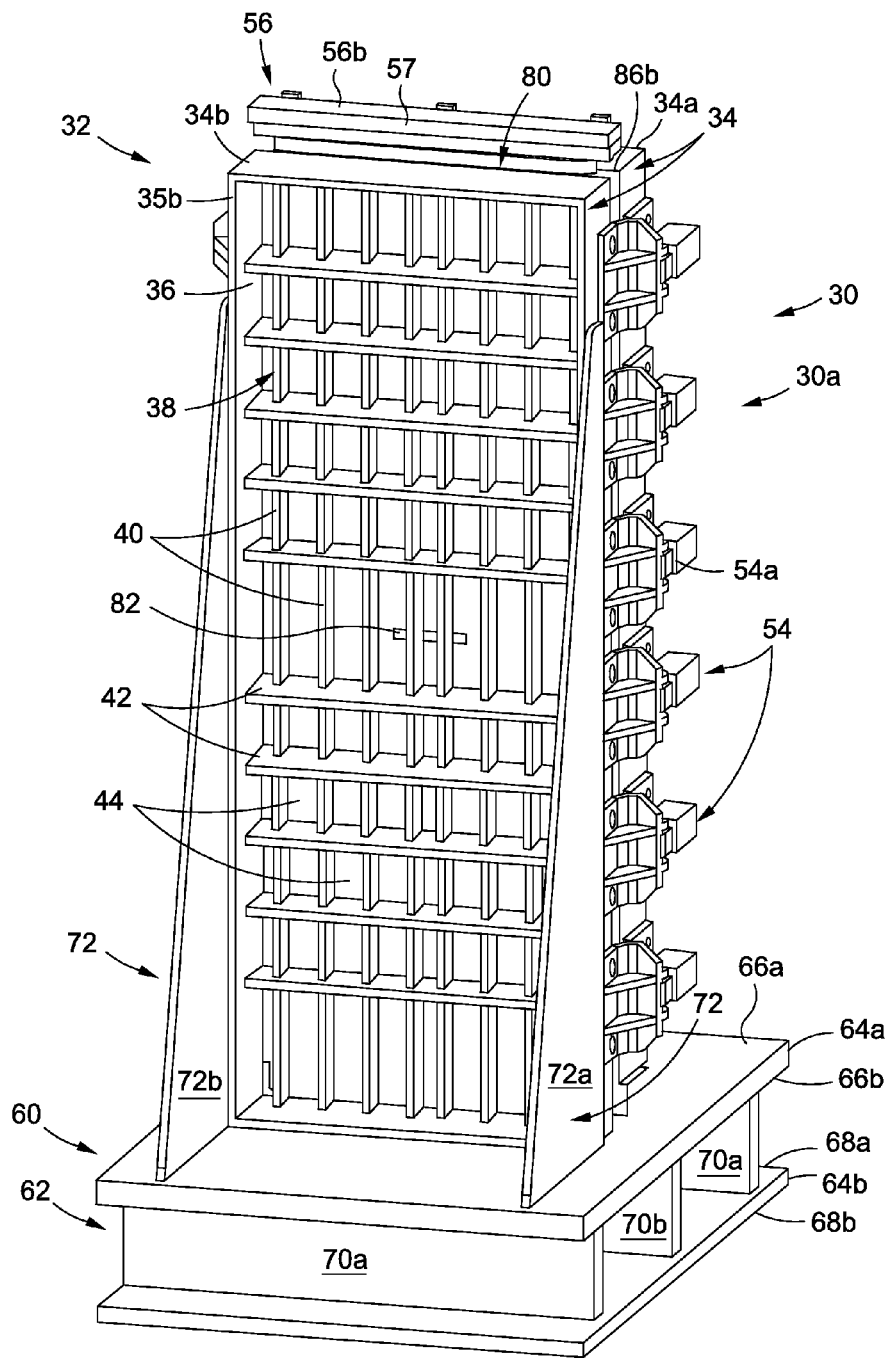
FIG. 2B is an illustration of a back perspective view of the apparatus of FIG. 2A.

Now referring to the Figures, FIG. 2A is an illustration of a front perspective view of an exemplary embodiment of an apparatus 30 for compression testing of a test specimen 80 (see FIG. 2H) of the disclosure. FIG. 2B is an illustration of a back perspective view of the apparatus 30 of FIG. 2A. As shown in FIGS. 2A-2B, the apparatus 30 may be in the form of a test fixture 30a, such as, for example, a large notch compression test fixture.

As shown in FIGS. 2A, 2H, the test specimen 80 may be in the form of a test panel 80a. The test panel 80a (see FIGS. 2A, 2H) may, for example, comprise a panel 220 (see FIG. 7), or part of a panel 220, of an aircraft 200a (see FIG. 7). The test specimen 80, such as in the form of test panel 80a, may be made of a composite material, or a metal material, such as aluminum or another suitable metal material. The test specimen 80 may also be in the form of a coupon, e.g., a flat piece of laminate, or another suitable test specimen preferably having a rectangular plan configuration and a rectangular cross section. As shown in FIG. 2H, the test specimen 80 preferably has a notch portion 82, discussed in further detail below.

As further shown in FIGS. 2A-2B, the apparatus 30 comprises a base assembly 60 having an end load element 74 attached to the base assembly 60. FIG. 2C is an illustration of a front perspective view of the base assembly 60 of the apparatus 30 of FIG. 2A. Preferably, the base assembly 60 (see FIG. 2A) is rigid and sturdy. Preferably, the base assembly 60 is made of a rigid material, such as steel or another suitable rigid metal material.

As shown in FIGS. 2A-2C, the base assembly 60 comprises a base platform 62. As further shown in FIGS. 2A-2C, the base platform 62 comprises a first platform portion 64a having a top side 66a and a bottom side 66b. As further shown in FIGS. 2A-2C, the base platform 62 comprises a second platform portion 64a having a top side 68a and a bottom side 68b.

As further shown in FIGS. 2A-2C, the base platform 62 comprises base support elements 70, for example, a first base support element 70a, a second base support element 70b, and a third base support element 70c. The base support elements 70 are preferably positioned between the first platform portion 64a and the second platform portion 64b, and are preferably spaced apart from each other.

The base assembly 60 further comprises side support portions 72 (see FIG. 2C). The side support portions 72 (see FIG. 2C) preferably comprise a first side support portion 72a (see FIG. 2C) opposite to and spaced from a second side support portion 72b (see FIG. 2C). The side support portions 72 (see FIG. 2C) are preferably attached to the top side 66a (see FIG. 2C) of the first platform portion 64a (see FIG. 2C) of the base platform 62 (see FIG. 2C).

Preferably, the side support portions 72 are made of a rigid material, such as steel or another suitable rigid metal material. The side support portions 72 provide support to a support assembly 32 (see FIG. 2A), and in particular, provide direct support to a second support grid 34b (see FIGS. 2A, 2E) of the support assembly 32 (see FIG. 2A).

Figure 2E:
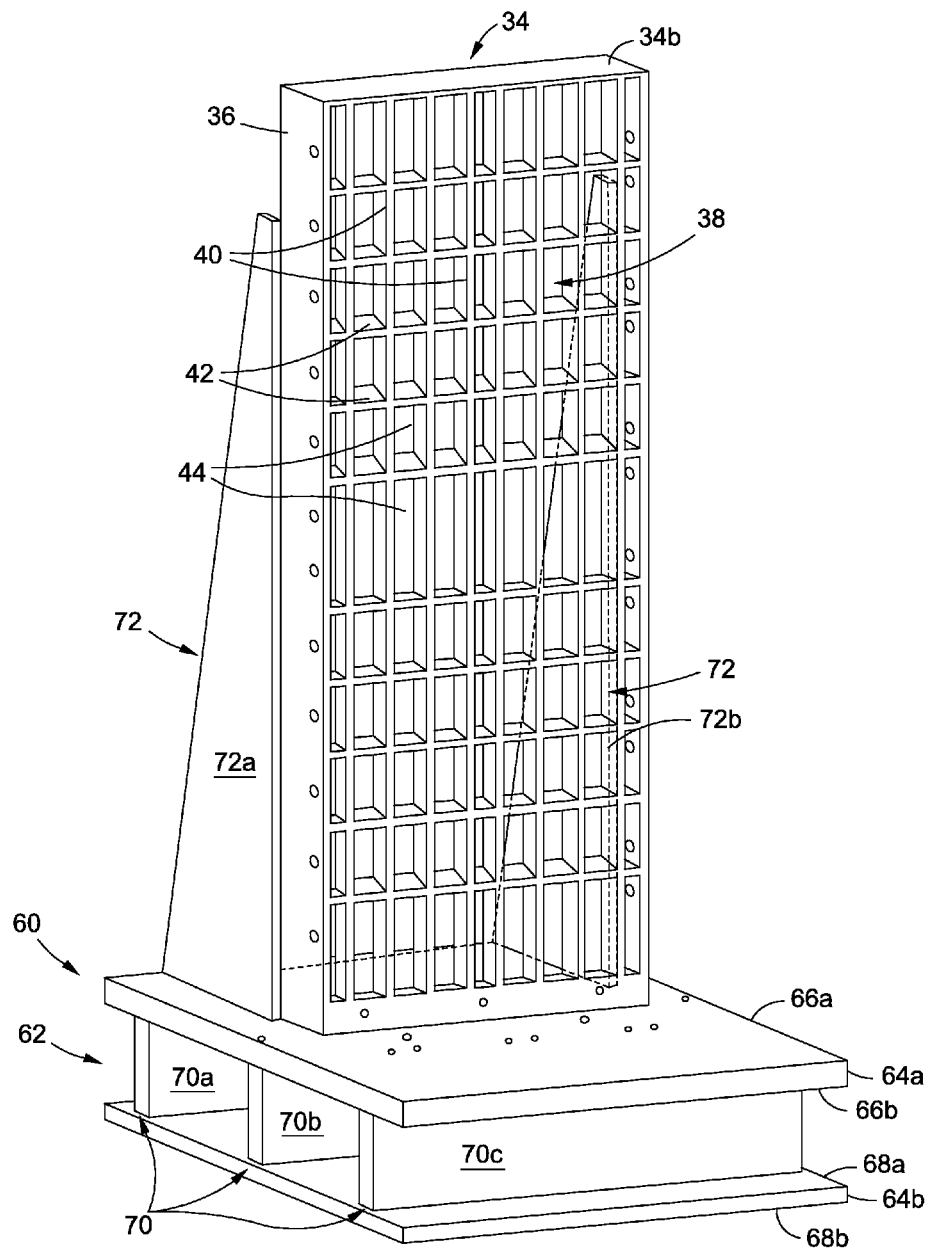
FIG. 2E is an illustration of a front perspective view of the support grid of FIG. 2D attached to the base assembly of FIG. 2C.
Figure 2F:
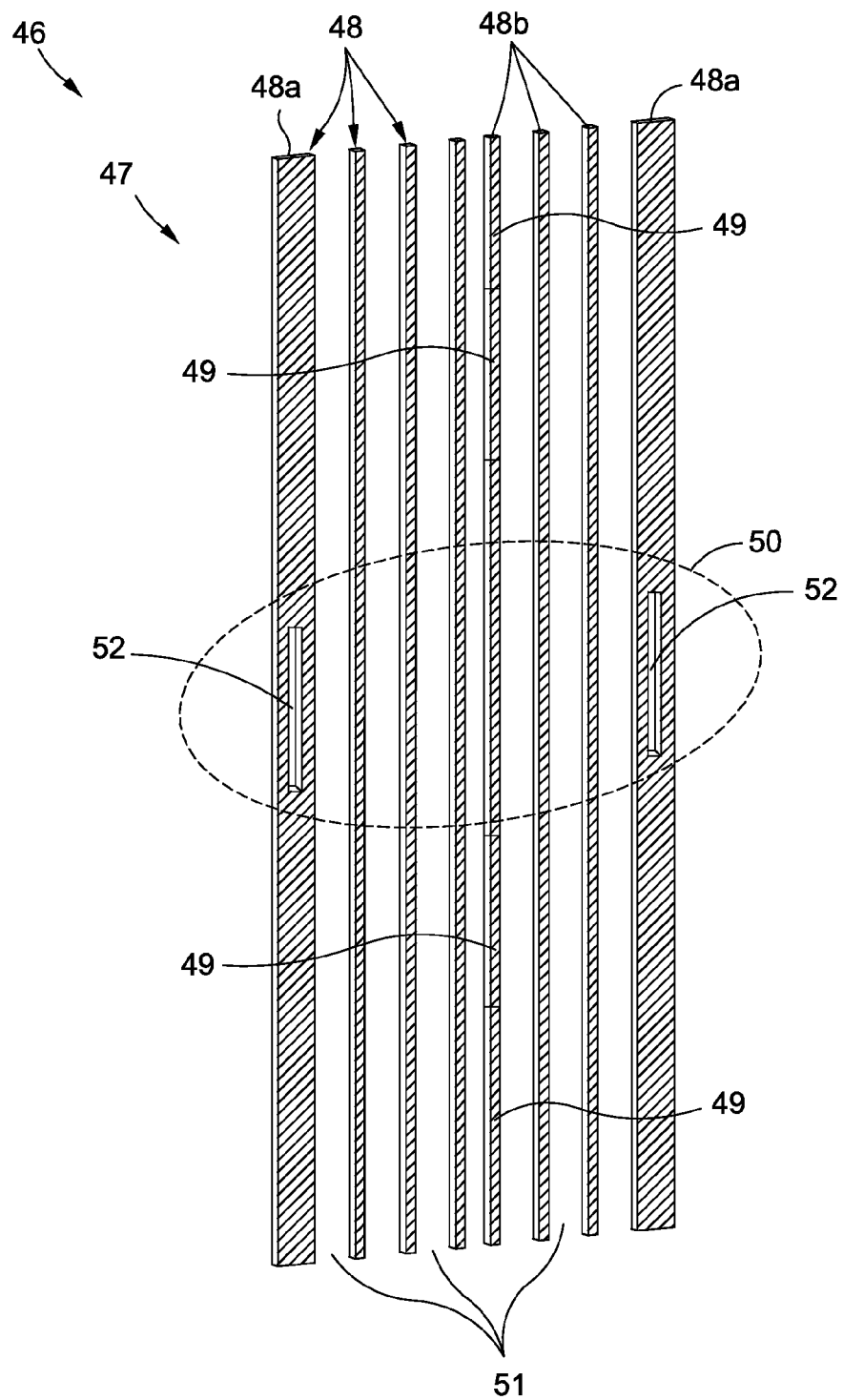
FIG. 2F is an illustration of a front perspective view of a core assembly used in the apparatus of FIG. 2A.
Figure 2G:
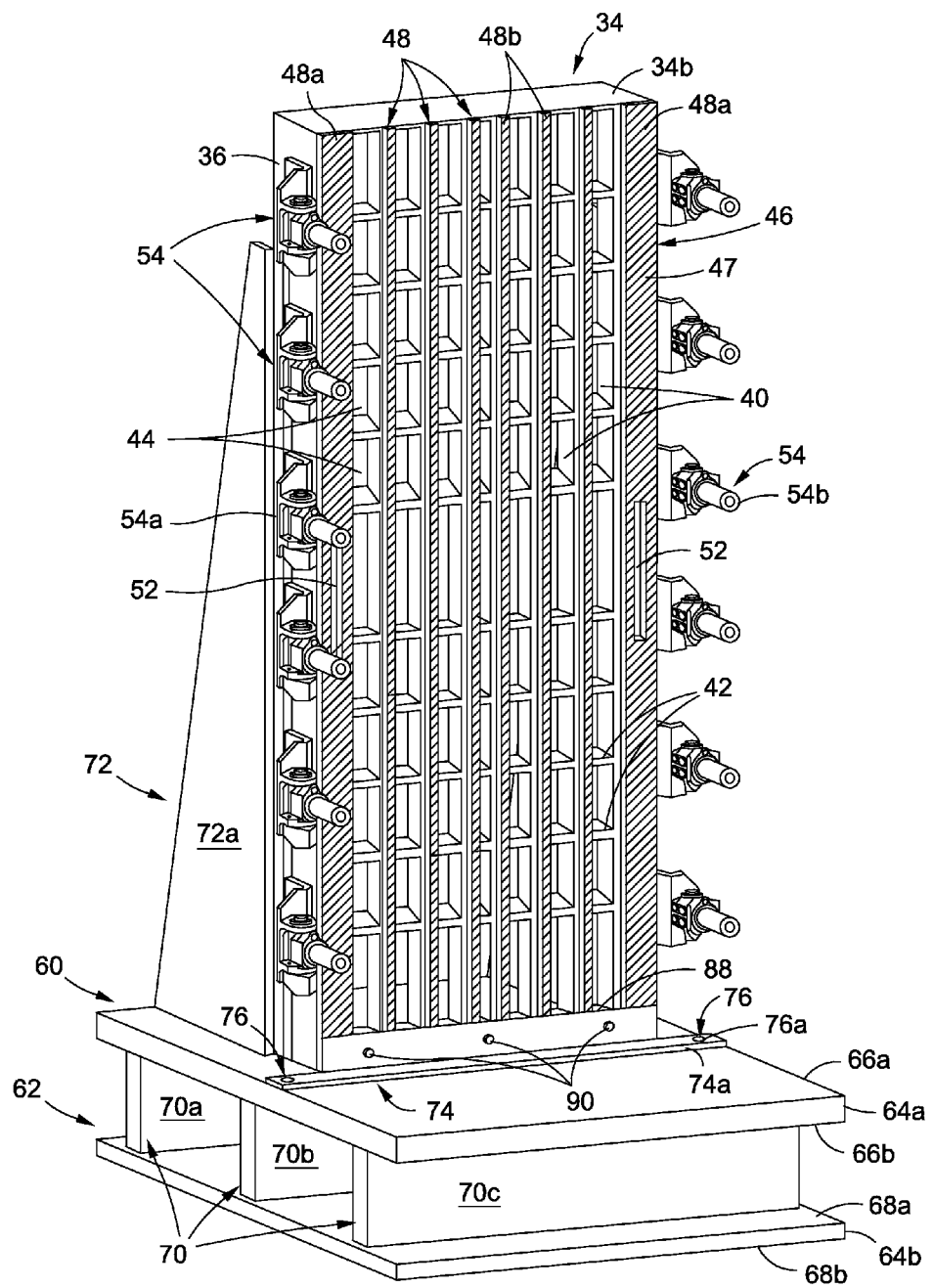
FIG. 2G is an illustration of a front perspective view of the core assembly of FIG. 2F attached to the support grid and the base assembly of FIG. 2E.

As shown in FIGS. 2A and 2G, the end load element 74 may be attached to the base assembly 60 between ends 78 (see FIG. 2A) and across the top side 66a (see FIG. 2G) of the first platform portion 64a. As shown in FIGS. 2A and 2G, the end load element 74 may be attached to the base assembly 60 with attachment elements 76, such as in the form of screws 76a or other suitable attachment elements. Preferably, the end load element 74 is in the form of an end load wear strip 74a (see FIGS. 2A, 2G).

The end load element 74 is preferably made of a metal material or other suitable material based on the particular compression testing conducted. For example, the end load element 74 may comprise a soft metal such as aluminum, copper, tin, or another soft metal, which may conform more easily. Alternatively, the end load element 74 may comprise a hard metal, which may be more durable. In addition, the end load element 74 may be made of a ceramic material, a plastic material, wood, or another suitable material that is durable and wear resistant.

The end load element 74 (see FIG. 2G) is preferably removable and replaceable, if damaged after testing. The end load element 74 (see FIG. 2G) may be replaced after one or more compression tests and is preferably configured to protect the base assembly 60 (see FIG. 2G) during compression testing. Preferably, the base assembly 60 is designed to withstand wear and tear over numerous compression tests, as compared to thin base structures of certain existing test fixtures.

As shown in FIGS. 2A-2B, the apparatus 30 further comprises a support assembly 32 attached to the base assembly 60. Preferably, the support assembly 32 is welded to the base assembly 60. However, other attachment means may be suitable.

As shown in FIGS. 2A-2B and FIGS. 2D-2E, the support assembly 32 comprises one or more support grids 34. FIG. 2D is an illustration of a front perspective view of a support grid 34 of the apparatus 30 of FIG. 2A. FIG. 2E is an illustration of a front perspective view of the support grid 34 of FIG. 2D attached to the base assembly 60 of FIG. 2C. The support grids 34 (see FIGS. 2A, 2E) are preferably made of a rigid material, such as steel or another suitably rigid metal.

As shown in FIGS. 2A, 2D, the support grids 34 preferably comprise a first support grid 34a and a second support grid 34b. The first support grid 34a is preferably situated in a front position. The second support grid 34b is preferably situated behind the first support grid 34a in a back position. The first support grid 34a is preferably configured for attachment to the second support grid 34b.

The first support grid 34a (see FIG. 2A) and the second support grid 34b (see FIG. 2E) each comprise a frame portion 36 (see FIGS. 2A, 2D) and a grid portion 38 (see FIGS. 2A, 2D). As shown in FIGS. 2A, 2D, each grid portion 38 comprises a plurality of vertical members 40, and a plurality of horizontal members 42 that intersect the plurality of vertical members 40. It should be appreciated that the terms "vertical" and "horizontal" describe the relative positions of the plurality of vertical members 40 (see FIGS. 2A, 2D) and the plurality of horizontal members 42 (see FIGS. 2A, 2D), for the sake of convenience and clarity, and may not be descriptive of their actual positions during compression testing.

As shown in FIGS. 2A-2B, the support assembly 32 has a plurality of window portions 44. The plurality of vertical members 40 (see FIGS. 2A-2B) and the plurality of horizontal members 42 (see FIGS. 2A, 2B) form the plurality of window portions 44 (see FIGS. 2A-2B). Preferably, the support grids 34 (see FIGS. 2A-2B) with the plurality of window portions 44 (see FIGS. 2A-2B) provide a see-through support system. Thus, the first support grid 34a (see FIG. 2A) and the second support grid 34b (see FIG. 2B) are preferably both see-through via their respective plurality of window portions 44 (see FIGS. 2A-2B).

Preferably, the first support grid 34a (see FIG. 2A) and the second support grid 34b (see FIG. 2B) may each have seventy (70) to eighty (80), or more, window portions 44. More preferably, the first support grid 34a (see FIG. 2A) and the second support grid 34b (see FIG. 2B) may each have seventy-seven (77) window portions 44.

The plurality of window portions 44 (see FIGS. 2A-2B) are preferably sized based on a thickness of the test specimen 80 (see FIG. 2H) and based on a width between adjacent vertical members 40 (see FIGS. 2A-2B). For example, each window portion 44 (see FIG. 2A) may have a width of about two (2) inches to about three (3) inches, and may have a length of about four (4) inches to about eight (8) inches. However, each window portion 44 may have a longer or shorter width and/or length.

The width between adjacent vertical members 40 may aid in the minimization or elimination of buckling of the test specimen 80 (see FIG. 2H) during compression testing. For example, a width from a centerline of one vertical member 40 to a centerline of an adjacent vertical member 40 may preferably be about one (1) inch to about three (3) inches apart, and more preferably, may be about one (1) inch apart.

As shown in FIGS. 2A-2B, the apparatus 30, such as in the form of text fixture 30a, may comprise a plurality of hinge elements 54 for attaching or coupling the first support grid 34a to the second support grid 34b. The hinge elements 54 (see FIG. 2A) may comprise a plurality of first side hinge elements 54a (see FIG. 2A) and a plurality of second side hinge elements 54b (see FIG. 2A). The hinge elements 54 are preferably spring loaded and may be made of a rigid material such as steel or another rigid metal. The hinge elements 54 may be configured with pins and clevis fittings so that the first support grid 34a may be opened like a door with respect to the second support grid 34b.

The apparatus 30 further comprises a core assembly 46 (see FIG. 2F) installed within the support assembly 32 (see FIG. 2A). FIG. 2F is an illustration of a front perspective view of the core assembly 46 used in the apparatus 30 of FIG. 2A. The core assembly (see FIG. 2F) is preferably crushable and configured to protect the support assembly 32 and the base assembly 60 from fracture loads 53 (see FIG. 5) generated during compression testing. Such fracture loads 53 (see FIG. 5) may be generated by a test specimen 80 (see FIG. 2H) positioned adjacent the core assembly (see FIG. 2F), when the test specimen 80 is fractured or broken during compression testing.

The core assembly 46 is designed to stabilize the test specimen 80 (see FIGS. 2A, 2H) during compression testing and is designed to crush and absorb energy that is released sideways from the test specimen 80 upon fracture or breaking of the test specimen 80 (see FIGS. 2A, 2H), such as at a notch portion 82 (see FIG. 2H). By absorbing fracture loads 53 (see FIG. 5) generated or produced from the fracture or breaking of the test specimen (see FIGS. 2A, 2H) during compression testing, the core assembly 46 primarily protects the surrounding support assembly 32 (see FIG. 2A), and also protects the base assembly 60.

The core assembly (see FIG. 2F) thus protects the support assembly 32 and the base assembly 60 from fracture loads 53 (see FIG. 5) or breaking loads, and in turn, may increase the life of the apparatus 30 (see FIG. 2A), such as the test fixture 30a (see FIG. 2A), and may allow a lighter weight apparatus 30 design. As used herein, "fracture load" means the load generated at the fracture or breaking point of the test specimen 80 (see FIG. 2H), and in particular, at the notch portion 82 (see FIG. 2H) of the test specimen (see FIG. 2H), when the test specimen 80 undergoes compression testing.

The core assembly 46 (see FIG. 2F) and the test specimen 80 (see FIG. 2H) are preferably installed between the first support grid 34a (see FIG. 2A) and the second support grid 34b (see FIG. 2A). The base assembly 60 (see FIG. 2A), the support assembly 32 (see FIG. 2A), and the core assembly 46 (see FIG. 2A) together comprise the apparatus 30 for compression testing of the test specimen 80 (see FIG. 2H) having a notch portion 82 (see FIG. 2H).

As shown in FIG. 2F, the core assembly 46 comprises a plurality of vertical core elements 48. It should be appreciated that the term "vertical" describes the relative position of the plurality of vertical core elements 48 (see FIG. 2F), for the sake of convenience and clarity, and may not be descriptive of their actual position during compression testing.

As further shown in FIG. 2F, the vertical core elements 48 may comprise end vertical core elements 48a and central vertical core elements 48b. FIG. 2F shows six (6) central vertical core elements 48b between two end vertical core elements 48a. However, more or less vertical core elements 48 may be used, depending on the testing conditions and testing machines used.

The end vertical core elements 48a (see FIG. 2F) preferably have a greater width than the central vertical core elements 48b (see FIG. 2F). For example, the end vertical core elements 48a (see FIG. 2F) may have a width of about two (2) inches to about four (4) inches, or more, and the central vertical core elements 48b (see FIG. 2F) may each have a width of about 0.5 inch to about one (1) inch. Each of the vertical core elements 48 may preferably have a thickness of about 0.5 inch.

In addition, as shown in FIG. 2F, each of the end vertical core elements 48a has an elongated slot 52. As shown in FIG. 2F, between each of the vertical core elements 48 is a space portion 51.

Each vertical core element 48 (see FIG. 2F) may comprise a honeycomb sandwich core assembly 47 (see FIG. 2F), comprising, for example, 0.5 inch thick aluminum facesheets and a core. Alternatively, each vertical core element 48 (see FIG. 2F) may comprise a rigid foam material or another suitably rigid material. Preferably, the vertical core elements 48 (see FIG. 2F) are sufficiently rigid to withstand compression loads of 300 kips (kilopounds force) per square inch of force, and more preferably, are sufficiently rigid to withstand compression loads in a range of about 300 kips (kilopounds force) per square inch of force to about 500 kips (kilopounds force) per square inch of force, or more.

As shown in FIG. 2F, the core assembly 46 has a crush zone 50. As shown in FIG. 2F, the crush zone 50 includes elongated slots 52 of the end vertical core elements 48a. The crush zone 50 preferably corresponds to a location 84 (see FIG. 2H) of the notch portion 82 (see FIG. 2H) in the test specimen 80 (see FIG. 2H), when the test specimen 80 (see FIG. 3A) is installed in an installation position 101 (see FIG. 3A) in the support assembly 32 (see FIG. 2A). For example, when the test specimen 80 (see FIG. 2A) is loaded, it is designed to fracture, break, or fail at the notch portion 82 (see FIG. 2A) and horizontally across the test specimen 80 (see FIG. 2A). This may result in excess movement normal to the surface of the test specimen 80 at the point of fracture, breakage, or failure. By providing a sufficient area to crush, such as with the crush zone 50 (see FIG. 2F), the apparatus 30 (see FIG. 2A) may be able to withstand increased loading.

The core assembly 46 (see FIG. 2F) is preferably sufficiently stiff so that it holds the test specimen 80, if the test specimen 80 starts buckling sideways during compression testing. However, when the test specimen 80 breaks, fractures, or fails upon compression testing, the impact and force of the test specimen 80 may locally crush one or more of the vertical core elements 48, particularly in the crush zone 50 (see FIG. 2F), of the core assembly 46, so that load does not get induced to the apparatus 30 (see FIG. 2A).

Each vertical core element 48 (see FIG. 2F) may be segmented and comprise one or more segments 49 (see FIGS. 2F, 2I), for example, one or more six (6) inch long segments, or another suitable length, that may be easily replaced with new vertical core elements 48 (see FIG. 2F) or new segments or portions that may be connected to the undamaged remaining segments of the vertical core elements 48 (see FIG. 2F). Thus, when the vertical core elements 48 each have segments 49 (see FIGS. 2F, 2I) in a segmented configuration, any damaged portion of the vertical core element 48 (see FIG. 2F) of the core assembly 46 (see FIG. 2F) may be easily replaced.

FIG. 2G is an illustration of a front perspective view of the core assembly 46 of FIG. 2F attached to the support grid 34, such as in the form of second support grid 34b, and attached to the base assembly 60 of FIG. 2E. As shown in FIG. 2G, the apparatus 30 may further comprise one or more grip plates 88. As further shown in FIG. 2G, the grip plate 88 is preferably attached across the bottom of the core assembly 46 with the bottom of the grip plate 88 adjacent the top side 66a of the base assembly 60. As shown in FIG. 2G, the grip plate 88 may be attached to the core assembly 46 with one or more attachment elements 90, such as screws or bolts, or another suitable attachment element.

The grip plate 88 (see FIG. 2G) may be attached or coupled to the core assembly 46 (see FIG. 2G) in a manner such that the first support grid 34a (see FIG. 2A) and the second support grid 34b (see FIG. 2A) may be spaced apart from each other slightly by a gap 86 (see FIG. 2A). As shown in FIG. 2A, the gap 86 may comprise a lower gap 86a and an upper gap 86b. With the presence of the gap 86 (see FIG. 2A), a slight movement together of an upper platen 104 (see FIG. 3A) and a lower platen 106 (see FIG. 3A) of a testing machine 102 (see FIG. 3A) may be allowed in order to test the compression strength of the test specimen 80 (see FIG. 3A) and to avoid reacting any of the compression loads 109 (see FIG. 5) through the apparatus 30 (see FIG. 3A).

As shown in FIG. 2G, the apparatus 30 may further comprise one or more grip fixtures 56, such as in the form of clamps 57. In order to support the test specimen 80 (see FIG. 2A) across the gap 86 (see FIG. 2A) and to prevent unwanted buckling of the test specimen 80 (see FIG. 2A) at the gap 86 (see FIG. 2A), one or more grip fixtures 56 (see FIG. 2A) may be attached to the test specimen 80 (see FIG. 2A).

As shown in FIG. 2A, the grip fixtures 56 may comprise a first grip fixture 56a and a second grip fixture 56b. The first grip fixture 56 (see FIG. 2A) is preferably coupled to the base assembly 60 (see FIG. 2A) and is configured to hold a first end 85a (see FIG. 2H) of the test specimen 80 (see FIG. 2H), when the test specimen 80 (see FIG. 2A) is installed in the support assembly 32 (see FIG. 2A).

As shown in FIG. 2A, the first grip fixture 56a may be coupled to the test specimen 80 (see FIG. 2A) via one or more attachment elements 58 (see FIG. 2A), such as in the form of bolts 58a (see FIG. 2A), or another suitable attachment element. The first grip fixture 58b is preferably configured to apply a pressure load 59 (see FIG. 5), such as a clamp load, across the first end 85a (see FIG. 2H) of the test specimen 80 (see FIGS. 2A, 2H).

As shown in FIGS. 2A-2B and 2H, the second grip fixture 58b is attached to the second end 85b (see FIG. 2H) of the test specimen 80. The second grip fixture 58b may be attached to the second end 85b of the test specimen 80 via one or more attachment elements 58, such as in the form of screws 58b, or another suitable attachment element. The second grip fixture 58b is preferably configured to apply a pressure load 59 (see FIG. 5), such as a clamp load, across the second end 85b (see FIG. 2H) of the test specimen 80 (see FIGS. 2A, 2H).

The apparatus 30 (sec FIG. 2A) is configured for use with an optical strain measurement system 120 (see FIG. 3A), discussed in detail below. When the test specimen 80 (see FIGS. 2H, 3A) is installed in the support assembly 32 (see FIG. 2A), the test specimen 80 (see FIGS. 2H, 3A) and the notch portion 82 (see FIGS. 2H, 3A) are visible to the optical strain measurement system 120 (see FIG. 3A) through the plurality of window portions 44 (see FIG. 2A).

Figure 3A:
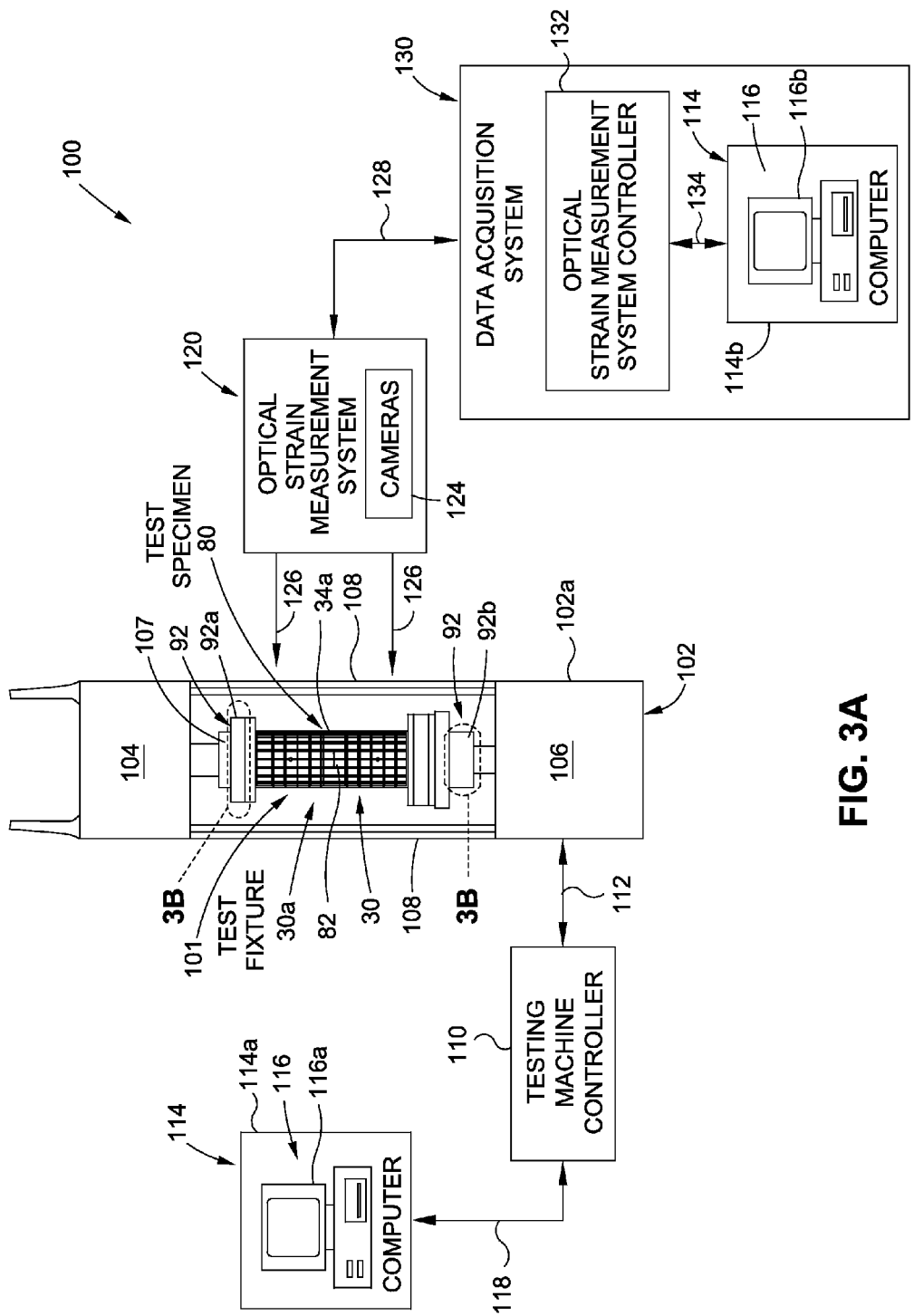
FIG. 3A is an illustration of a schematic diagram of an exemplary embodiment of a system for compression testing of the disclosure.
Figure 5:
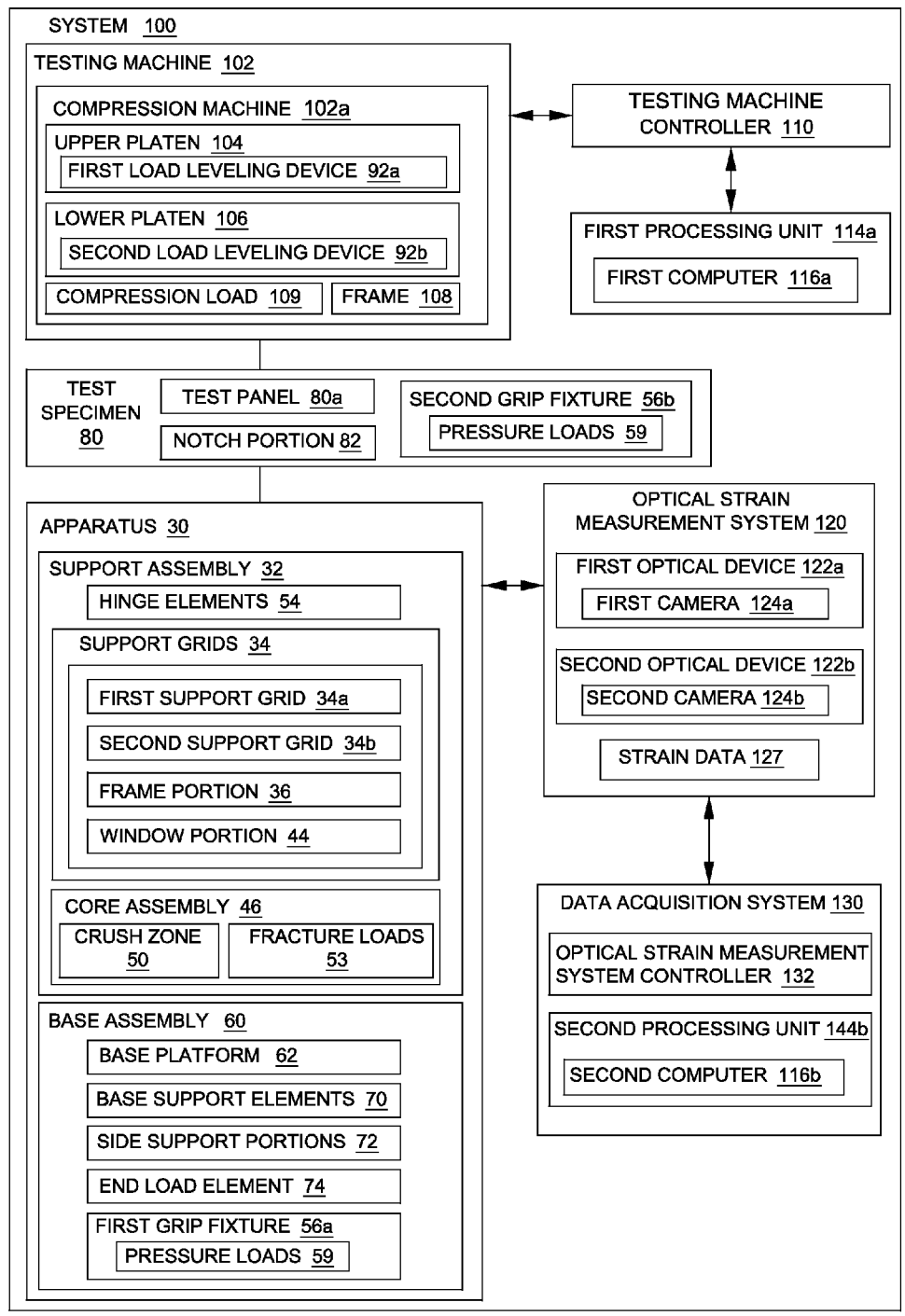
FIG. 5 is an illustration of a block diagram of an embodiment of a system and an apparatus for compression testing of the disclosure.

In another embodiment of the disclosure, there is provided a system 100 for compression testing. FIG. 5 is an illustration of a block diagram of an embodiment of the system 100 for compression testing that includes the apparatus 30 for compression testing discussed above. FIG. 3A is an illustration of a schematic diagram of an exemplary embodiment of the system 100 for compression testing of the disclosure.

As shown in FIGS. 3A and 5, the system 100 comprises the apparatus 30 for compression testing. The apparatus 30 may be in the form of a test fixture 30a (see FIG. 3A). As discussed in detail above, the apparatus 30 (see FIGS. 3A, 5) comprises a base assembly 60 (see FIG. 5) having an end load element 74 (see FIG. 5) attached to the base assembly 60 (see FIG. 5). The apparatus 30 (see FIG. 5) further comprises a support assembly 32 (see FIG. 5) attached to the base assembly 60 (see FIG. 5). The support assembly 32 has a plurality of window portions 44 (see FIG. 5).

The apparatus 30 (see FIG. 5) further comprises a core assembly 46 (see FIG. 5) installed within the support assembly 32 (see FIG. 5). The core assembly 46 is preferably crushable and designed to absorb fracture load energy upon fracture or breaking of the test specimen 80 (see FIGS. 2A, 2H), such as at the notch portion 82 (see FIG. 2H). The core assembly 46 (see FIG. 5) and the test specimen 80 (see FIG. 5) are preferably installed between the first support grid 34a (see FIG. 5) and the second support grid 34b (see FIG. 5).

As shown in FIGS. 2H, 3A and 5, the system 100 further comprises a test specimen 80 having a notch portion 82. FIG. 2H is an illustration of a front perspective view of the test specimen 80 used in the apparatus 30 of FIG. 2A. The test specimen 80 (see FIG. 2H) is preferably installed in the support assembly 32 (see FIG. 5) of the apparatus 30 (see FIG. 5). As shown in FIGS. 3A and 3C, the test specimen 80, is in an installed position 101 in the apparatus 30 and in the testing machine 102.

As shown in FIG. 2H, the test specimen 80 may be in the form of a test panel 80a. The test panel 80a may, for example, comprise a panel 220 (see FIG. 7), or part of a panel 220, of an aircraft 200a (see FIG. 7). The test specimen 80, such as in the form of test panel 80a, may be made of a composite material, or a metal material, such as aluminum or another suitable metal material. The test specimen 80 may also be in the form of a coupon, e.g., a flat piece of laminate, or another suitable test specimen preferably having a rectangular plan configuration and a rectangular cross section. The test specimen 80, such as in the form of test panel 80a, may preferably have a width of about twenty (20) inches wide, a length of about sixty (60) inches, and a thickness of about 0.25 inch to about 0.10 inch thick. However, the test specimen 80 may also be of another suitable width, length, or thickness, depending on the testing conditions and testing machines used.

As shown in FIG. 2H, the test specimen 80 has a first end 85a that is preferably adjacent the base assembly 60 (see FIG. 2I) when the test specimen 80 is installed in the apparatus 30 (see FIG. 2A). As shown in FIG. 2H, the test specimen 80 has a second end 85b that is preferably attached to the grip fixture 56, such as in the form of the second grip fixture 56b, discussed above.

As shown in FIG. 2H, the notch portion 82 of the test specimen 80 is formed at a location 84 in the test specimen 80, preferably a central location. The notch portion 82 (see FIG. 3C) is preferably perpendicular to a direction 109a (see FIG. 3C) of the one or more compression loads 109 (see FIG. 5) applied by the testing machine 102 (see FIG. 3C) to the test specimen 80 (see FIG. 3C). The notch portion 82 may preferably have a width of about four (4) inches wide and a thickness of about 0.25 inch to about 0.10 inch thick. However, the notch portion 82 may be of another suitable width or thickness depending on the testing conditions.

FIG. 2I is an illustration of a front perspective view of the test specimen 80 of FIG. 2H installed in front of the core assembly 46 (see FIG. 2G) and installed on the base assembly 60 of FIG. 2E. As shown in FIG. 2I, the test specimen 80 is installed over the core assembly 46 (see FIG. 2G), such as in the form of honeycomb sandwich core assembly 47, and over the second support grid 34b.

As shown in FIGS. 3A, 3C and 5, the system 100 further comprises a testing machine 102, such as in the form of a compression machine 102a. FIG. 3C is an illustration of a front perspective view of the apparatus 30 of FIG. 2A installed in an exemplary embodiment of the testing machine 102, such as in the form of compression machine 102a, that may be used in the system 100 of FIG. 3A. The compression machine 102a may comprise, for example, an MTS machine manufactured by MTS Corporation of Minneapolis, Minn. However, other suitable testing machines 102 may be used.

As shown in FIGS. 3A and 3C, the testing machine 102, such as in the form of compression machine 102a, comprises an upper platen 104, a lower platen 106, a frame 108, a load cell 107 (see FIG. 3A), and feet 146 (see FIG. 3C). The upper platen 104 and the lower platen 106 may be movable between a closed position as shown in FIG. 3A and an open position as shown in FIG. 3C.

Figure 2J:
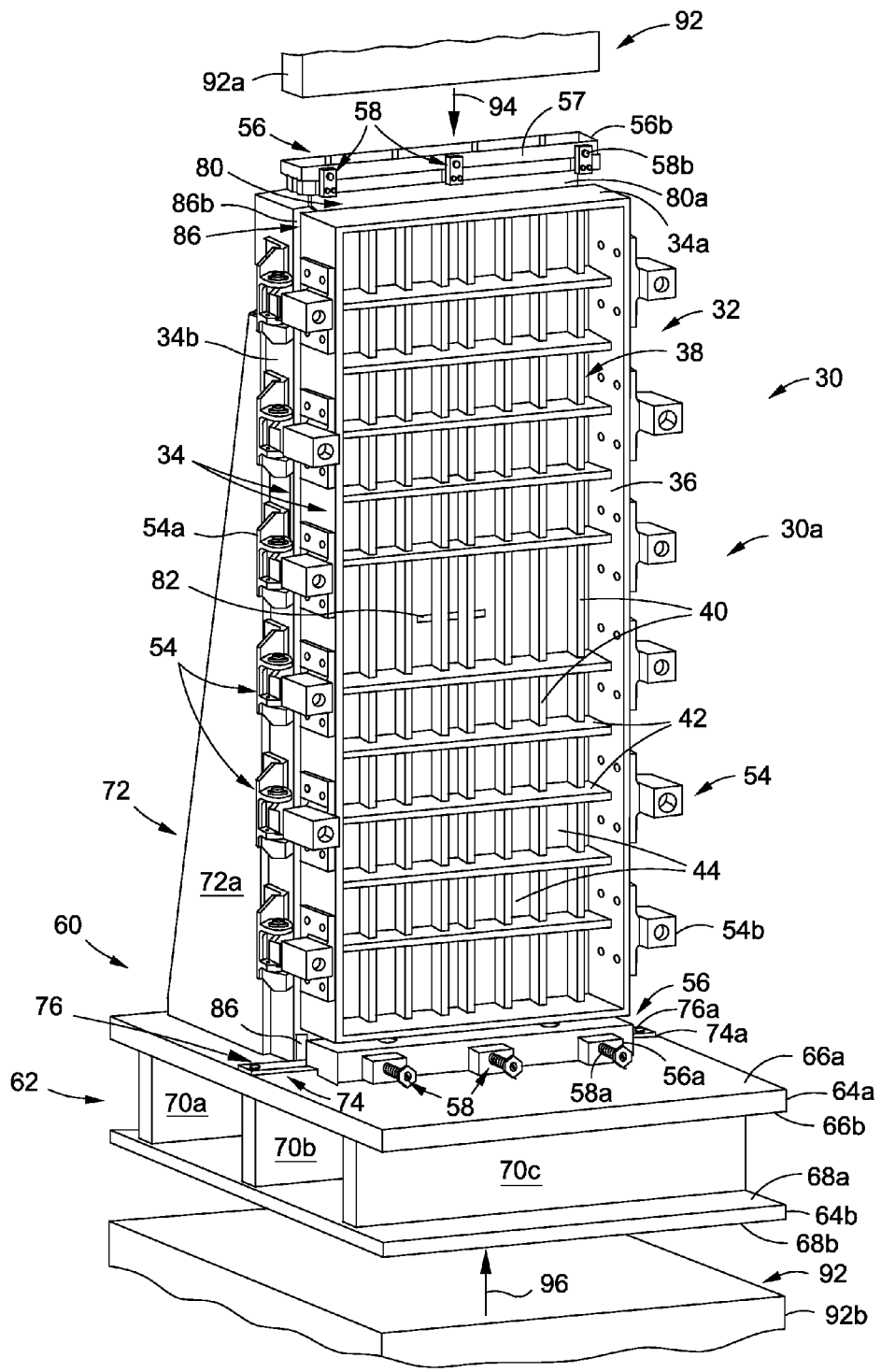
FIG. 2J is an illustration of a front perspective view of the apparatus of FIG. 2A showing use with load leveling devices.

FIG. 2J is an illustration of a front perspective view of the apparatus 30 of FIG. 2A showing use with load leveling devices 92. As shown in FIG. 2J, a first load leveling device 92a may be coupled to the second grip fixture 56b by coupling the first load leveling device 92a in a downward direction indicated by arrow 94 to the second grip fixture 56b. Alternatively, the first load leveling device 92a (see FIG. 3B) may be used in place of the second grip fixture 56b (see FIG. 2A) and coupled to the second end 85b (see FIG. 2H) of the test specimen 80 (see FIG. 2H).

As further shown in FIG. 2J, a second load leveling device 92b may be coupled to the base assembly 60 by coupling the second load leveling device 92b in an upward direction indicated by arrow 96 to the base assembly 60. Alternatively, the second load leveling device 92b may be coupled to the first grip fixture 56a, or the second load leveling device 92b may be used in place of the first grip fixture 56a and coupled to the first end 85a (see FIG. 2H) of the test specimen 80 (see FIG. 2H).

As shown in FIG. 3A, the one or more load leveling devices 92 may be coupled to the apparatus 30 installed in the testing machine 102. The load leveling devices 92 preferably assist in self-alignment, self-balancing or self-leveling of the test specimen 80 and the apparatus 30. In one embodiment, as shown in FIG. 3A, the arrangement may comprise the upper platen 104 of the testing machine 102, the first load leveling device 92a, the test fixture 30a, the second load leveling device 92b, and the lower platen 106 of the testing machine 102.

As shown in FIG. 3A, a first load leveling device 92a may be coupled to the top of the apparatus 30, such as in the form of test fixture 30a (see FIG. 3A). Alternatively, the first load leveling device 92a (see FIG. 3B) may be used in place of the second grip fixture 56b (see FIG. 2A). The first load leveling device 92a (see FIG. 3B) may be coupled or attached to the first one to two inches of the second end 85b (see FIG. 2H) of the test specimen 80 to keep the loaded edge of the test specimen 80 from brooming or spreading out when compression loads 109 (see FIG. 5) are applied to the test specimen 80 during compression testing.

Alternatively, or in addition, to the first load leveling device 92a, a second load leveling device 92b may be coupled to the bottom of the apparatus 30, or alternatively, the second load leveling device 92b may be coupled to the first grip fixture 56a (see FIG. 2A) or used in place of the first grip fixture 56a (see FIG. 2A). The load leveling devices 92 balance the load to ensure the first end 85a (see FIG. 2H) and second end 85b (see FIG. 2H) of the test specimen 80 (see FIG. 2H) are loaded at any point along the long end of the test specimen 80 (see FIG. 2H). The load leveling devices 92 help to prevent or minimize the loaded edges of the test specimen 80 from brooming or spreading out when loaded in compression during compression testing.

Figure 3B:
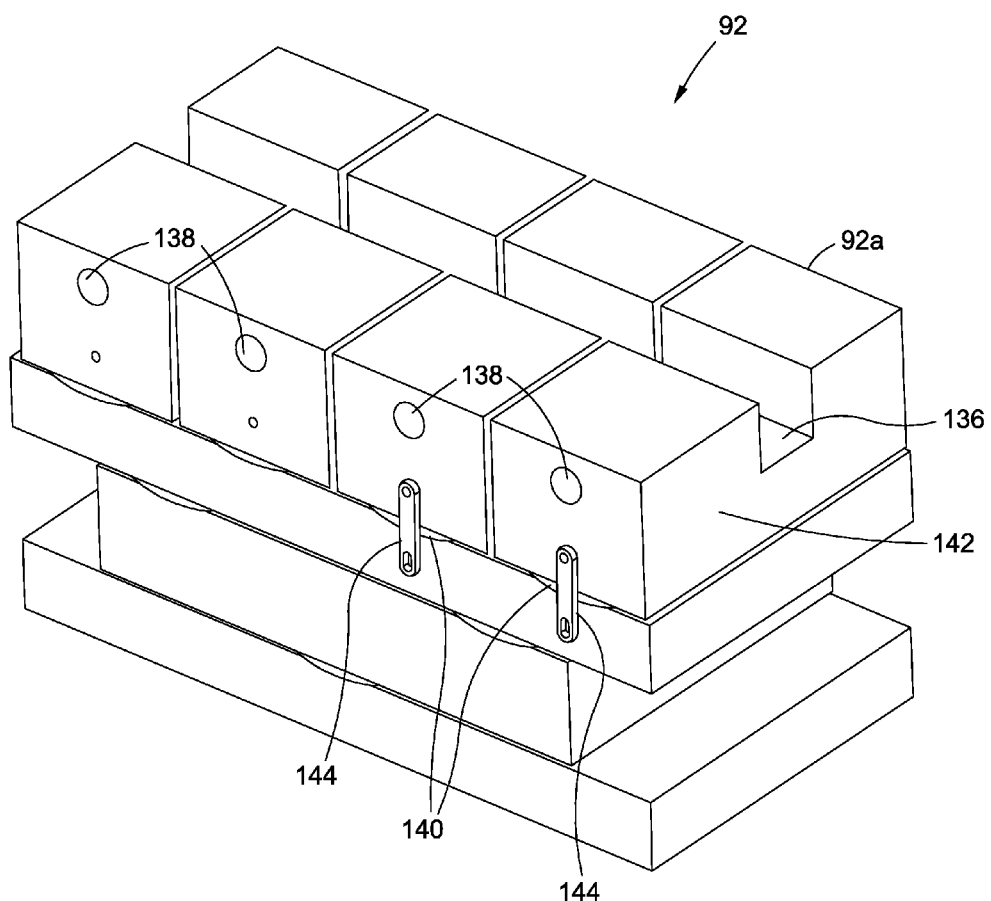
FIG. 3B is an illustration of a front perspective view of an exemplary embodiment of a load leveling device that may be used in the system of FIG. 3A.
Figure 3C:
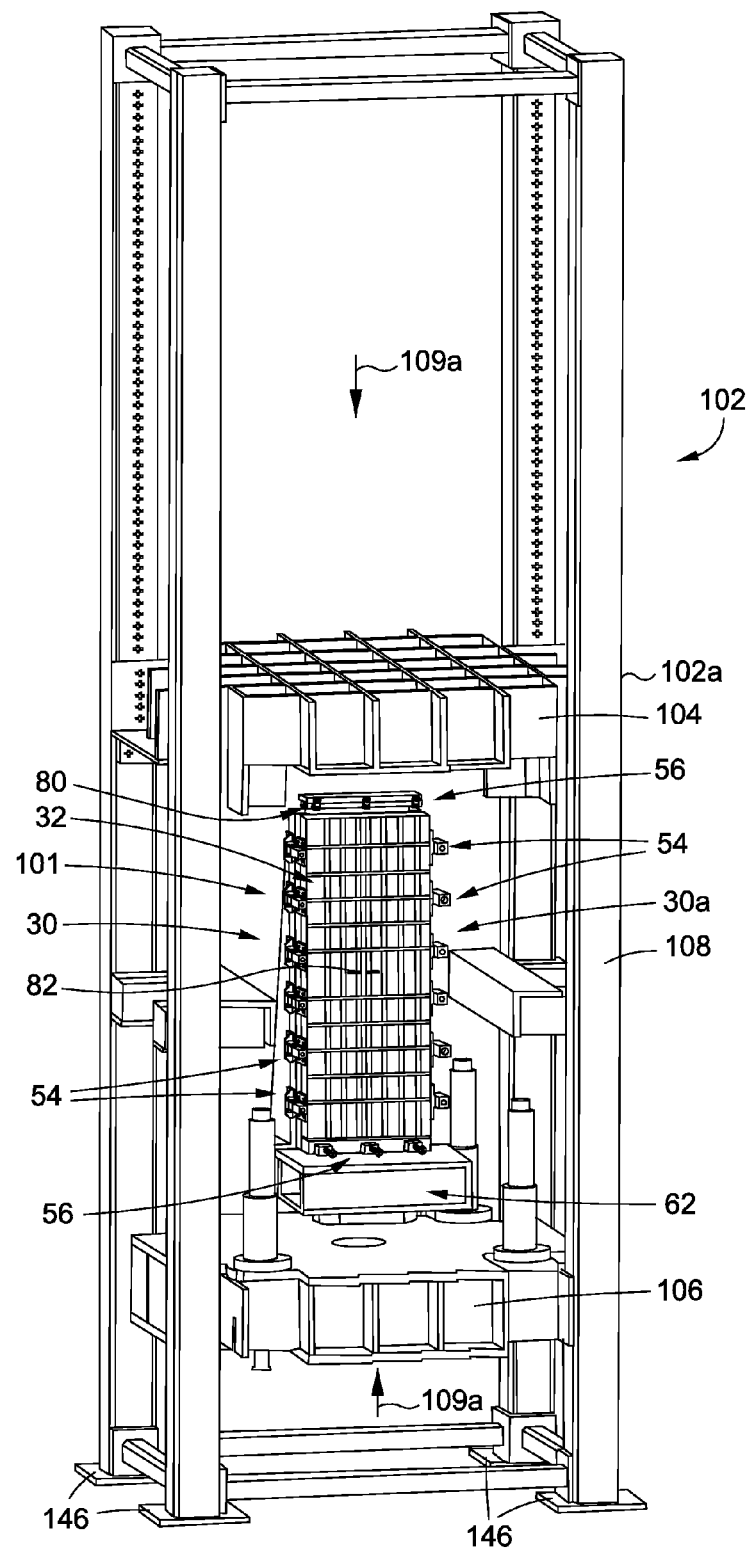
FIG. 3C is an illustration of a front perspective view of the apparatus of FIG. 2A installed in an exemplary embodiment of a testing machine that may be used in the system of FIG. 3A.

FIG. 3B is an illustration of a front perspective view of an exemplary embodiment of the load leveling device 92, such as in the form of first load leveling device 92a, that may be used in the system 100 of FIG. 3A. The first load leveling device 92a may be used in place of second grip fixture 56b (see FIG. 2A). As shown in FIG. 3B, the load leveling device 92 comprises an alignment portion 142 having a slot 136 for insertion of the test specimen 80 (see FIG. 3A). As further shown in FIG. 3B, the load leveling device 92 may comprise openings 138 configured for receiving attachment elements (not shown), such as screws (not shown), that may be used to clamp down on the test specimen 80 (see FIG. 3A).

As further shown in FIG. 3B, the load leveling device 92 may comprise one or more round elements 140 that may allow the attachment elements (not shown) to move or float up and down. Such movement may facilitate self-alignment, self-balancing or self-leveling of the test specimen 80 and the apparatus 30. As further shown in FIG. 3B, the load leveling device 92, such as in the form of first load leveling device 92a, may comprise link members 144 that assist in holding the load leveling device 92 together during compression testing.

As shown in FIG. 3C, the testing machine 102, such as in the form of compression machine 102a, is preferably configured to apply one or more compression loads 109 (see FIG. 5) to the test specimen 80, in direction 109a, when the apparatus 30 with the test specimen 80 is installed in the testing machine 102. As shown in FIG. 3C, the notch portion 82 of the test specimen 80 is visible.

As shown in FIGS. 3A and 5, the system 100 further comprises a testing machine controller 110 coupled to the testing machine 102 and configured to control operation of the testing machine 102. The testing machine controller 110 may be coupled to the testing machine 102 by a connection element 112, such as a suitable wired or wireless connection.

As shown in FIGS. 3A and 5, the system 100 may further comprise a processing unit 114, such as a first processing unit 114a, coupled to the testing machine controller 110 via a connection element 112. The connection element 118 may comprise a suitable wired or wireless connection. As shown in FIGS. 3A and 5, the processing unit 114 may comprise a computer 116, such as a first computer 116a.

As shown in FIGS. 3A and 5, the system 100 further comprises an optical strain measurement system 120 positioned in relation to the apparatus 30 with the test specimen 80 installed in the apparatus 30 and the apparatus 30 installed in the testing machine 102. As shown in FIG. 3A, the apparatus 30 with the test specimen 80 is preferably installed in the testing machine 102, so that the test specimen 80 and the notch portion 82 are visible to the optical strain measurement system 120 through the plurality of window portions 44 (see FIG. 4C-4D). The first support grid 34a (see FIG. 3C) of the apparatus 30 (see FIG. 3A) preferably faces front toward the optical strain measurement system 120 (see FIG. 3A).

The optical strain measurement system 120 (see FIGS. 3A, 4A-4B) preferably comprises two or more optical devices 122 (see FIGS. 4A-4B). The optical devices 122 may comprise a first optical device 122a (see FIG. 4A) and a second optical device 122b (see FIG. 4A).

The optical strain measurement system 120 is preferably a camera based system in which the optical devices 122 are in the form of cameras 124 (see FIGS. 4A-4B). The cameras 124 monitor and track a plurality of locations 152 (see FIGS. 4A-4B), such as in the form of dots or points, on the surface of the test specimen 80 (see FIGS. 4A-4B). The cameras 124 may comprise a first camera 124a (see FIG. 4A) and a second camera 124b (see FIG. 4A). However, other suitable optical devices 122 may be used.

The optical strain measurement system 120 preferably comprises two or more optical devices 122 configured to both capture and scan optical measurements 126 (see FIGS. 3A, 4A-4B) at a plurality of locations 152 (see FIGS. 4A-4B) on the surface of the test specimen 80 (see FIGS. 4A-4B) installed in the apparatus 30 (see FIG. 4A). An example of an optical strain measurement system 120 that may be used includes the Aramis Optical 3D Deformation Analysis optical strain measurement system obtained from GOM mbH of Germany. However, other suitable optical strain measurement systems may also be used.

The optical strain measurement system 120 may be used to determine material properties of a test specimen 80 (see FIG. 2H), may be used to obtain strain data 127 (see FIG. 5), such as for example, surface strain values, buckling strain, and strain rates, may be used to obtain three-dimensional displacements and surface coordinates, and may be used to obtain other suitable data. The optical strain measurement system 120 may be used to capture and evaluate the measuring area efficiently and with good accuracy. Suitable software may be used with the optical strain measurement system 120 to provide results for optical measurements 126 (see FIGS. 3A, 4A-4B) at a plurality of locations 152 (see FIGS. 4A-4B) on the surface of the test specimen 80 (see FIGS. 4A-4B).

FIG. 4A is an illustration of a side view of an exemplary embodiment of an optical strain measurement system 120 that may be used in the system 100 of FIG. 3A. FIG. 4A shows the optical strain measurement system 120 positioned in front of the apparatus 30. As shown in FIG. 4A, the first optical device 122a, such as in the form of a first camera 124a, is positioned in front of the upper half of the first support grid 34a of the apparatus 30. As further shown in FIG. 4A, the first optical device 122a, such as in the form of first camera 124a, is positioned to capture and scan optical measurements 126, such as upper horizontal optical measurements 126a at a plurality of locations 152 (see FIG. 4A) on the surface of the test specimen 80 (see FIG. 4A) installed in the apparatus 30.

As further shown in FIG. 4A, the second optical device 12M, such as in the form of a second camera 124b, is positioned in front of the lower half of the first support grid 34a of the apparatus 30. As shown in FIG. 4A, the second optical device 122b, such as in the form of the second camera 124b, is positioned to capture and scan optical measurements 126, such as lower horizontal optical measurements 126b, at a plurality of locations 152 (see FIG. 4A) on the surface of the test specimen 80 (see FIG. 4A) installed in the apparatus 30.

As shown in FIG. 4A, the first camera 124a is preferably above a centerline 150 between the first camera 124a and the second camera 124b. The second camera 124b is preferably below the centerline 150. The first camera 124a and the second camera 124b may be positioned a sufficient distance from the test specimen 80 (see FIG. 3A) installed in the apparatus 30. Preferably, the first camera 124a and the second camera 124b may be positioned a distance 151 (see FIG. 4B) of about ten (10) feet from the apparatus 30. However, the first camera 124a and the second camera 124b may be positioned a longer or shorter distance from the apparatus 30.

FIG. 4A shows the first camera 124a positioned a distance 148 above the second camera 124b. Preferably, the first camera 124a may be positioned about 15 inches above the centerline 150 between the first camera 124a and the second camera 124b. Preferably, the second camera 124b may be positioned about 15 inches below the centerline 150 between the first camera 124a and the second camera 124b. However, the first camera 124a and the second camera 124b may be positioned a longer or shorter distance above or below the centerline 150.

FIG. 4B is an illustration of a top view of the optical strain measurement system 120 of FIG. 4A positioned in front of the first support grid 34a of the apparatus 30. As shown in FIG. 4B, the optical device 122 comprising first optical device 122a, such as in the form of camera 124, is positioned in front of the upper half of the first support grid 34a of the apparatus 30. As further shown in FIG. 4B, the first optical device 122a, such as in the form of camera 124, is positioned to capture and scan optical measurements 126, such as upper vertical optical measurements 126c and lower vertical optical measurements 126d, at a plurality of locations 152 (see FIG. 4B) on the surface of the test specimen 80 (see FIG. 4B) installed in the apparatus 30.

Figure 4C:
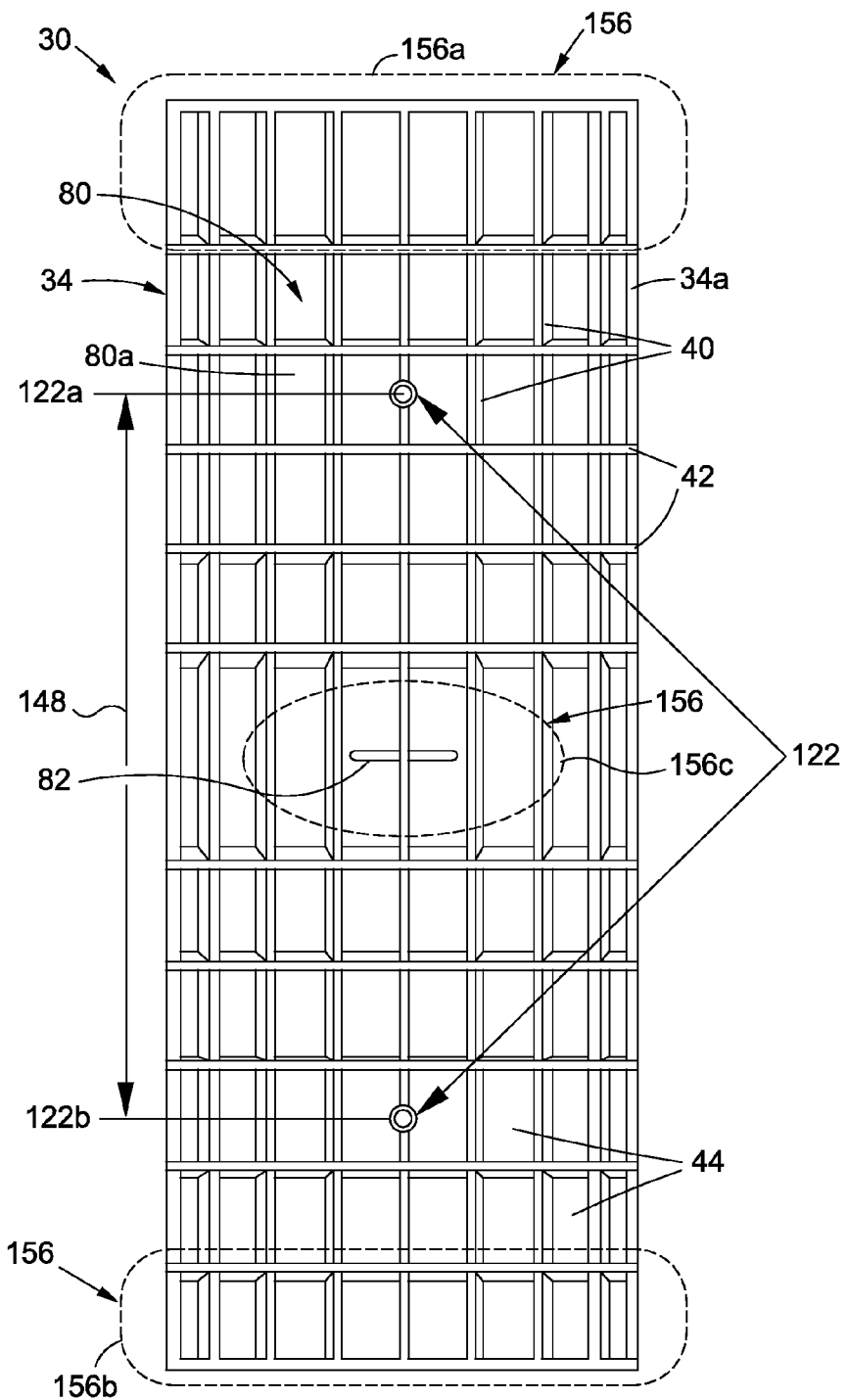
FIG. 4C is an illustration of a front perspective view of the apparatus of FIG. 4A showing camera focal points of the optical strain measurement system of FIG. 4A.

FIG. 4C is an illustration of a front perspective view of the apparatus 30 of FIG. 4A showing optical devices 122, such as in the form of first optical device 122a and second optical device 122b, of the optical strain measurement system 120 of FIG. 4A. The optical devices 122, preferably in the form of cameras 124 (see FIGS. 4A-4B), are preferably focused on the test specimen 80, such as in the form of test panel 80a.

FIG. 4C shows that a load balance 156, such as in the form of a load balance 156a indicated by an upper dotted circle, is viewed and measured with the first optical device 122a, such as first camera 124a (see FIG. 4A) or upper camera. FIG. 4C further shows that a load balance 156, such as in the form of a load balance 156b indicated by a lower dotted circle, is viewed and measured with the second optical device 122b, such as second camera 124b (see FIG. 4A) or lower camera.

FIG. 4C shows that a load balance 156, such as in the form of a load balance 156c indicated by a middle dotted circle, is viewed and measured with both the first optical device 122a, such as first camera 124a (see FIG. 4A) or upper camera, and the second optical device 122b, such as second camera 124b (see FIG. 4A) or lower camera. As shown in FIG. 4C, the notch portion 82 is within the load balance 156*c* indicated by middle dotted circle.

Figure 4D:
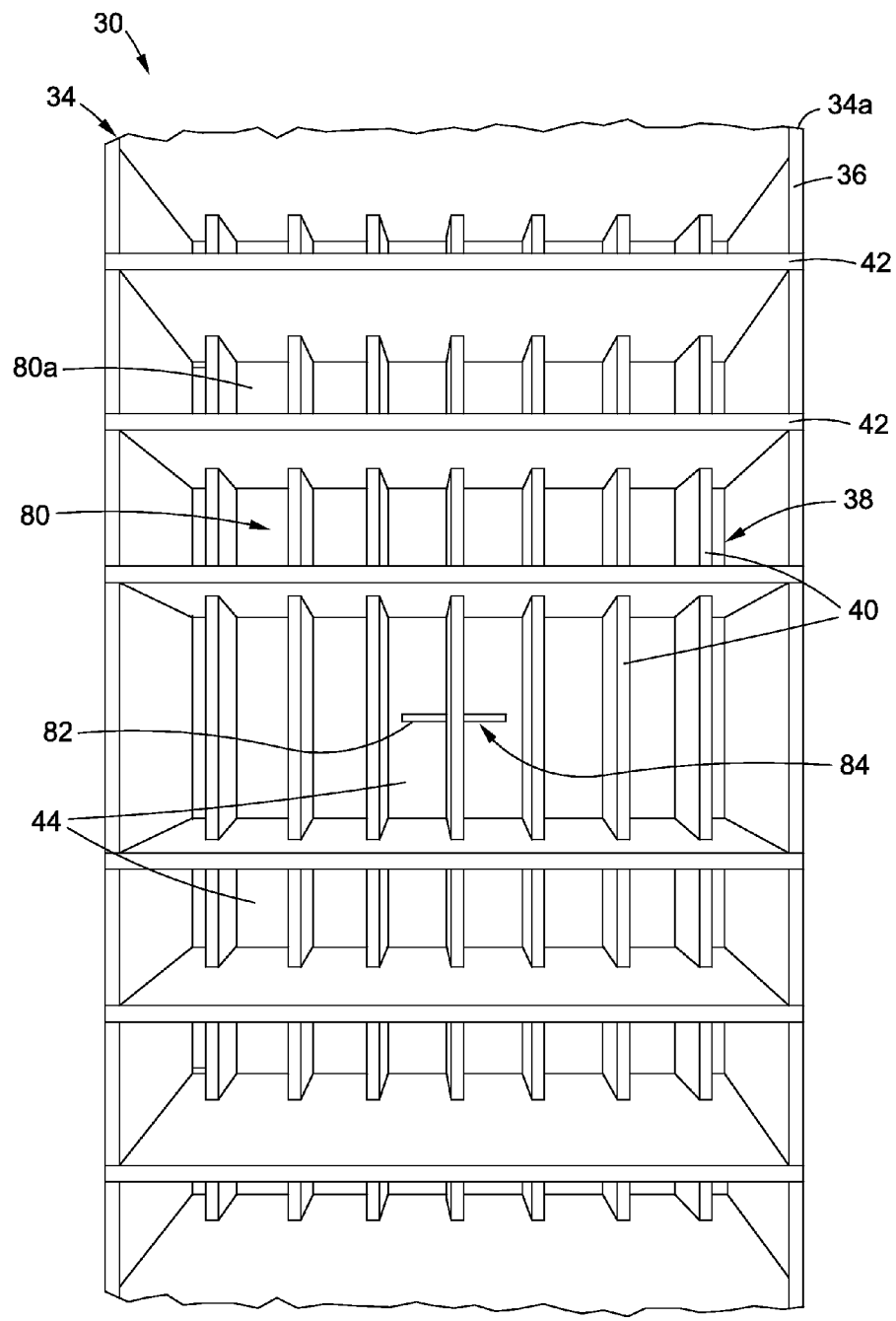
FIG. 4D is an illustration of a close-up, front perspective view of a support grid showing a notch portion visible through window portions.

FIG. 4D is an illustration of a close-up, front perspective view of the support grid 34, such as in the form of first support grid 34*a*, of the apparatus 30. FIG. 4D shows the test specimen 80, such as in the form of test panel 80*a*, and the notch portion 82 at location 84, visible through the window portions 44. As shown in FIG. 4D, the notch portion 82 is positioned centrally between vertical members 40 and horizontal members 42.

As shown in FIGS. 3A and 5, the system 100 further comprises a data acquisition system 130 coupled to the optical strain measurement system 120 via a connection element 128. The connection element 128 may comprise a suitable wired or wireless connection.

As shown in FIGS. 3A and 5, the data acquisition system 130 may comprise an optical strain measurement system controller 132 and a processing unit 114, such as a second processing unit 114*b*. As shown in FIGS. 3A and 5, the processing unit 114 may comprise a computer 116, such as a second computer 116*b*.

As shown in FIG. 3A, the strain measurement system controller 132 may be coupled to the second processing unit 114*b* via a connection element 134. The connection element 134 may comprise a suitable wired or wireless connection.

The apparatus 30 (see FIG. 5), the test specimen 80 (see FIG. 5), the testing machine 102 (see FIG. 5), the testing machine controller 110 (see FIG. 5), the optical strain measurement system 120 (see FIG. 5), and the data acquisition system 130 (see FIG. 5) together comprise the system 100 (see FIG. 5) for compression testing of the test specimen 80 (see FIG. 5).

As shown in FIG. 5, the support assembly 32 comprises a first support grid 34*a* configured for attachment to a second support grid 34*b*. The first support grid 34*a* and the second support grid 34*b* each comprise a frame portion 36, a plurality of vertical members 40, and a plurality of horizontal members 42. The plurality of vertical members 40 (see FIG. 2A) and the plurality of horizontal members 42 (see FIG. 2A) form the plurality of window portions 44 (see FIG. 2A).

Figure 6:
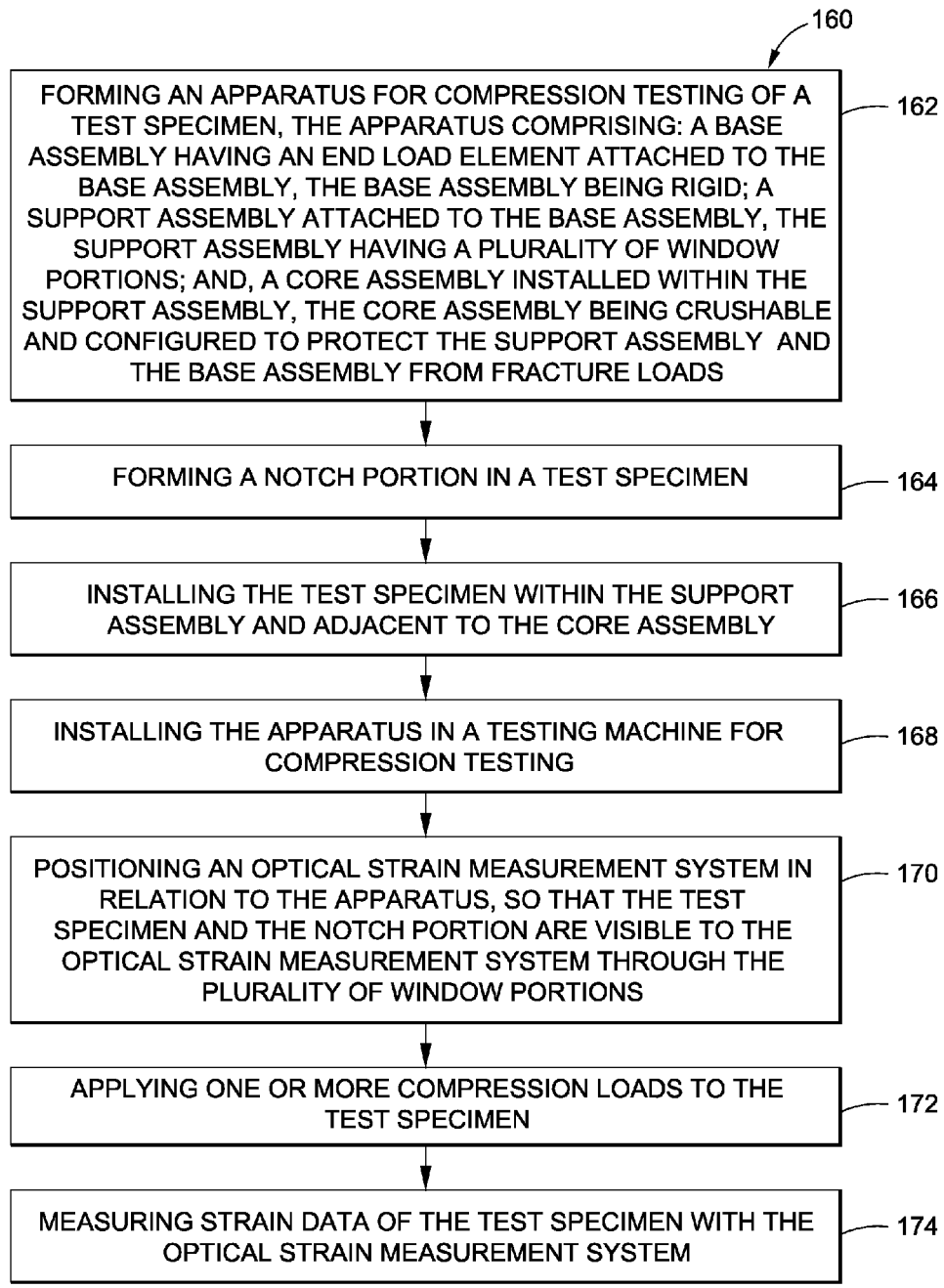
FIG. 6 is an illustration of a flow diagram of an exemplary embodiment of a method of the disclosure.

In another embodiment of the disclosure, there is provided a method 160 (see FIG. 6) for compression testing of a test specimen 80 (see FIG. 2H). FIG. 6 is an illustration of a flow diagram of an exemplary embodiment of the method 160 of the disclosure. As shown in FIG. 6, the method 160 comprises step 162 of forming an apparatus 30 (see FIG. 2A) for compression testing of the test specimen 80 (see FIG. 2H).

As discussed in detail above, the apparatus 30 (see FIG. 2A) comprises a base assembly 60 (see FIG. 2A) having an end load element 74 (see FIG. 2A) attached to the base assembly 60 (see FIG. 2A). The base assembly 60 (see FIG. 2A) is preferably rigid and sturdy.

The apparatus 30 (see FIG. 2A) further comprises a support assembly 32 (see FIG. 2A) attached to the base assembly 60 (see FIG. 2A). The support assembly 32 (see FIG. 2A) has a plurality of window portions 44 (see FIG. 2A).

The apparatus 30 further comprises a core assembly 46 (see FIG. 2F) installed within the support assembly 32 (see FIG. 2A). The core assembly (see FIG. 2F) is preferably crushable and configured to protect the support assembly 32 and the base assembly 60 from fracture loads 53 (see FIG. 5) generated during compression testing. Such fracture loads 53 (see FIG. 5) may be generated by a test specimen 80 (see FIG. 2H) positioned adjacent to the core assembly (see FIGS. 2F, 2I), when the test specimen 80 fractures or breaks during compression testing of the test specimen 80. The compression loads 109 (see FIG. 5) that may occur during compression testing of the test specimen 80 (see FIG. 2H) may be in a range of about 300 kips (kilopounds force) per square inch of force to about 500 kips (kilopounds force) per square inch of force. However, the compression loads 109 may be higher or lower as suitable.

As shown in FIG. 6, the method 160 further comprises step 164 of forming a notch portion 82 (see FIG. 2H) in a test specimen 80 (see FIG. 2H). As shown in FIG. 6, the method 160 further comprises step 166 of installing the test specimen 80 (see FIG. 2H) within the support assembly 32 (see FIG. 2A) and adjacent to the core assembly 46 (see FIGS. 2F, 2I).

As shown in FIG. 6, the method 160 further comprises step 168 of installing the apparatus 30 (see FIG. 2A) in a testing machine 102 (see FIG. 3A), such as a compression machine 102*a*, for compression testing. The step 168 of installing the apparatus 30 (see FIG. 2A) in the testing machine 120 (see FIG. 3A) may comprise coupling one or more load leveling devices 92 (see FIG. 3A) to the apparatus 30 (see FIG. 3A).

As shown in FIG. 6, the method 160 further comprises step 170 of positioning an optical strain measurement system 120 (see FIG. 3A) in relation to the apparatus 30 (see FIG. 3A). The optical strain measurement system 120 (see FIG. 3A) is positioned so that the test specimen 80 (see FIG. 3A) and the notch portion 82 (see FIG. 3A) are visible to the optical strain measurement system 120 (see FIG. 3A) through the plurality of window portions 44 (see FIG. 4C).

As shown in FIG. 6, the method 160 further comprises step 172 of applying one or more compression loads 109 (see FIG. 5) to the test specimen 80 (see FIG. 3C) in directions 109*a* (see FIG. 3C). The one or more compression loads 109 (see FIG. 3C) are preferably applied to the test specimen 80 (see FIG. 3C) via the upper platen 104 (see FIG. 3C) and the lower platen 106 (see FIG. 3C) of the testing machine 102, such as in the form of compression machine 102*a*.

As shown in FIG. 6, the method 160 further comprises step 174 of measuring strain data 127 (see FIG. 5) of the test specimen 80 (see FIG. 3A) with the optical strain measurement system 120 (see FIG. 3A). The step 174 of measuring the strain data 127 comprises using two or more optical devices 122 (see FIGS. 4A-4B) to capture and scan optical measurements 126 (see FIGS. 4A-4B) at a plurality of locations 152 (see FIGS. 4A-4B) on the test specimen 80 (see FIGS. 4A-4B).

The method 160 may further comprise after step 174, the step of processing the strain data 127 (see FIG. 5) with the data acquisition system 130 (see FIG. 3A) to determine additional information relating to strain, such as buckling strain, or other material characteristics, of the test specimen 80 (see FIG. 3A). After the strain data 127 (see FIG. 5) has been processed, if additional compression testing is conducted, the end load element 74 (see FIG. 2A) may be removed and replaced on the base assembly 60 (see FIG. 2A), if damaged. In addition, any damaged portions of the core assembly 46 (see FIG. 2F) may be replaced on the core assembly 46 (see FIG. 2F).

Figure 7:
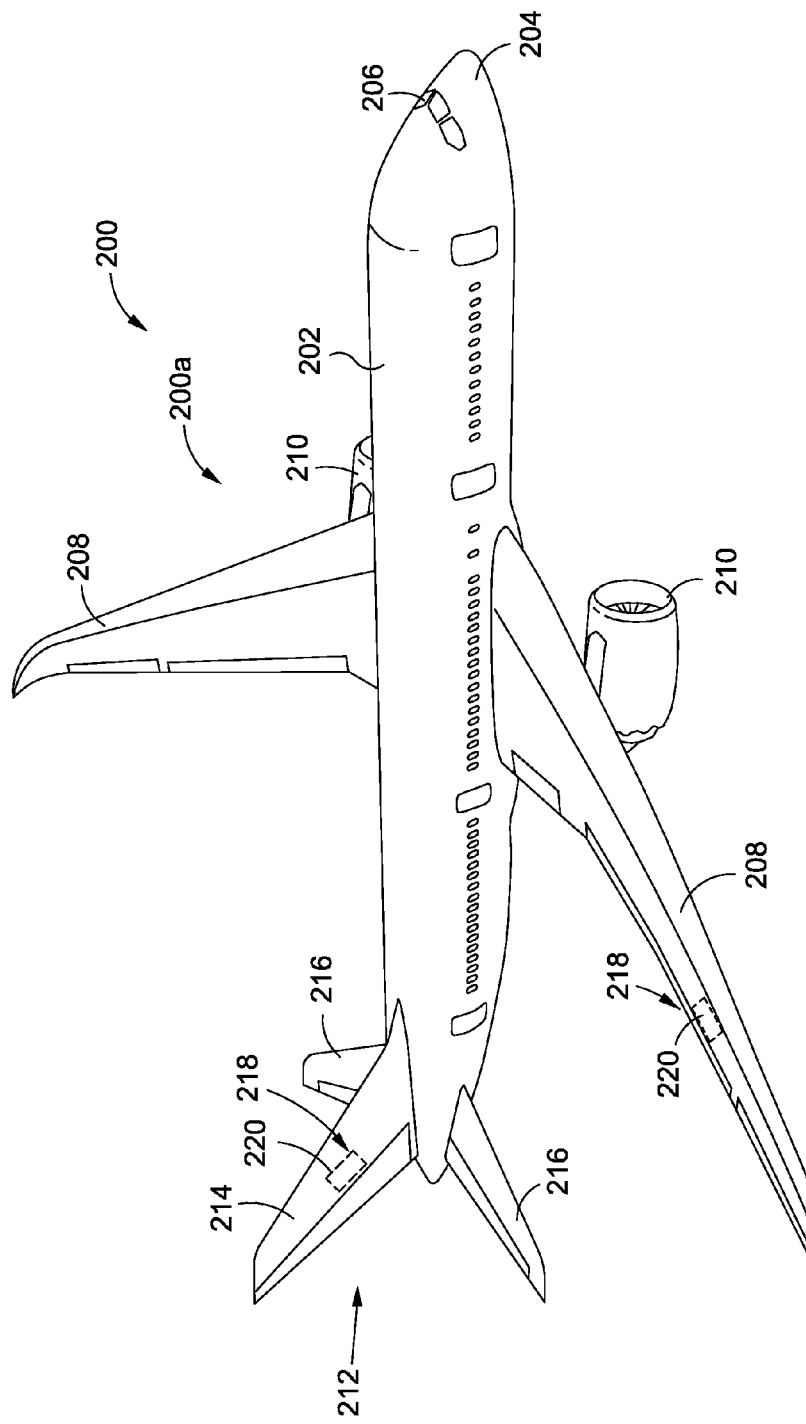
FIG. 7 is an illustration of a perspective view of an aircraft having one or more structures that may be tested and evaluated with embodiments of an apparatus, a system and a method of the disclosure.

FIG. 7 is an illustration of a perspective view of an air vehicle 200, such as an aircraft 200*a*, having one or more structures 218, such as in the form of a panel 220, that may be tested and evaluated with embodiments of the apparatus 30 (see FIG. 2A), the system 100 (see FIG. 5) and the method 160 (see FIG. 6) of the disclosure, as discussed in detail above. As shown in FIG. 7, the air vehicle 200, such as in the form of aircraft 200*a*, comprises a fuselage 202, a nose 204, a cockpit 206, wings 208, one or more propulsion units 210, and a tail 212 comprising a vertical tail portion 214 and horizontal tail portions 216.

Although the aircraft 200*a* shown in FIG. 7 is generally representative of a commercial passenger aircraft having one or more structures 218, such as in the form of panel 220, the teachings of the disclosed embodiments may be applied to other passenger aircraft. For example, the teachings of the disclosed embodiments may be applied to cargo aircraft, military aircraft, rotorcraft, and other types of aircraft or aerial vehicles, as well as aerospace vehicles, satellites, space launch vehicles, rockets, and other aerospace vehicles.

Figure 8:
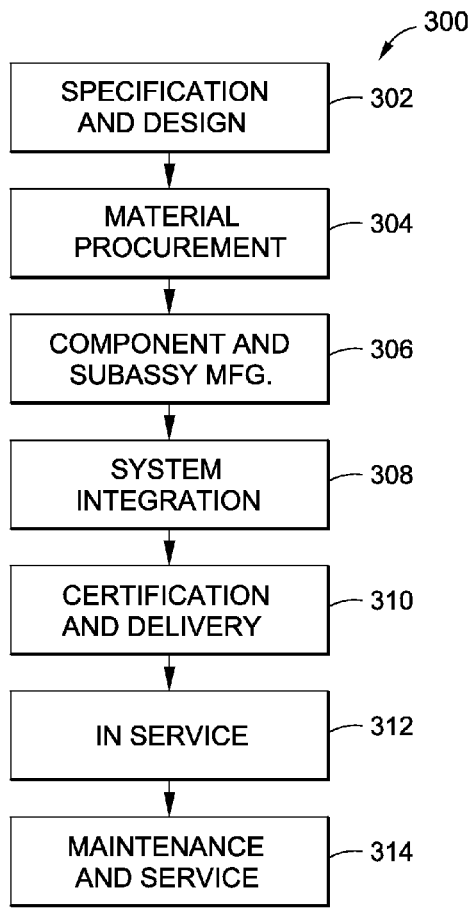
FIG. 8 is an illustration of a flow diagram of an aircraft manufacturing and service method; and, FIG. 9 is an illustration of a functional block diagram of an embodiment of an aircraft of the disclosure.
Figure 9:
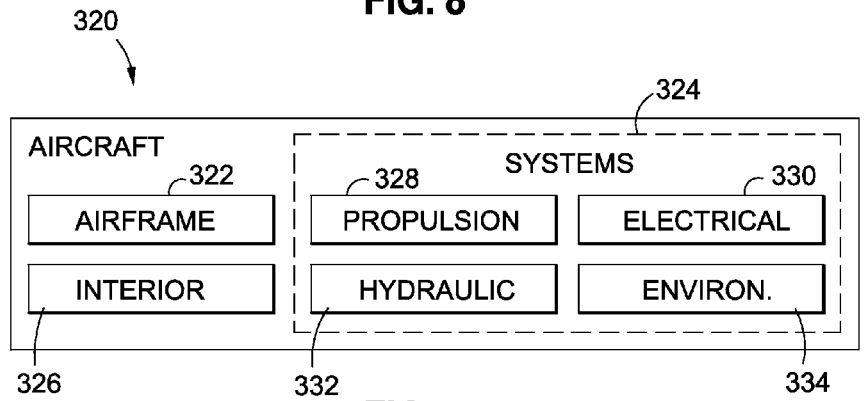

FIG. 8 is an illustration of a flow diagram of an aircraft manufacturing and service method 300. FIG. 9 is an illustration of a functional block diagram of an embodiment of an aircraft 320 of the disclosure. Referring to FIGS. 8-9, embodiments of the disclosure may be described in the context of the aircraft manufacturing and service method 300 as shown in FIG. 8, and the aircraft 320 as shown in FIG. 9.

During pre-production, exemplary aircraft manufacturing and service method 300 may include specification and design 302 of the aircraft 320 and material procurement 304. During manufacturing, component and subassembly manufacturing 306 and system integration 308 of the aircraft 320 takes place. Thereafter, the aircraft 320 may go through certification and delivery 310 in order to be placed in service 312. While in service 312 by a customer, the aircraft 320 may be scheduled for routine maintenance and service 314 (which may also include modification, reconfiguration, refurbishment, and other suitable services).

Each of the processes of the aircraft manufacturing and service method 300 may be performed or carried out by a system integrator, a third party, and/or an operator (e.g., a customer). For the purposes of this description, a system integrator may include, without limitation, any number of aircraft manufacturers and major-system subcontractors. A third party may include, without limitation, any number of vendors, subcontractors, and suppliers. An operator may include an airline, leasing company, military entity, service organization, and other suitable operators.

As shown in FIG. 9, the aircraft 320 produced by the exemplary aircraft manufacturing and service method 300 may include an airframe 322 with a plurality of systems 324 and an interior 326. Examples of the plurality of systems 324 may include one or more of a propulsion system 328, an electrical system 330, a hydraulic system 332, and an environmental system 334. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 300. For example, components or subassemblies corresponding to component and subassembly manufacturing 306 may be fabricated or manufactured in a manner similar to components or subassemblies produced while the aircraft 320 is in service 312. Also, one or more apparatus embodiments, method embodiments, or a combination thereof, may be utilized during component and subassembly manufacturing 306 and system integration 308, for example, by substantially expediting assembly of or reducing the cost of the aircraft 320. Similarly, one or more of apparatus embodiments, method embodiments, or a combination thereof, may be utilized while the aircraft 320 is in service 312, for example and without limitation, to maintenance and service 314.

Disclosed embodiments of the apparatus 30 (see FIG. 2A), system 100 (see FIGS. 3A, 5), and method 160 (see FIG. 6) enable testing to be performed on test specimens 80 (see FIG. 2H), such as in the form of test panels 80*a* (see FIG. 2H), at a much higher test rate than testing using certain existing test fixtures. This is due to the reduced time needed for test set-up and testing.

Figure 1:
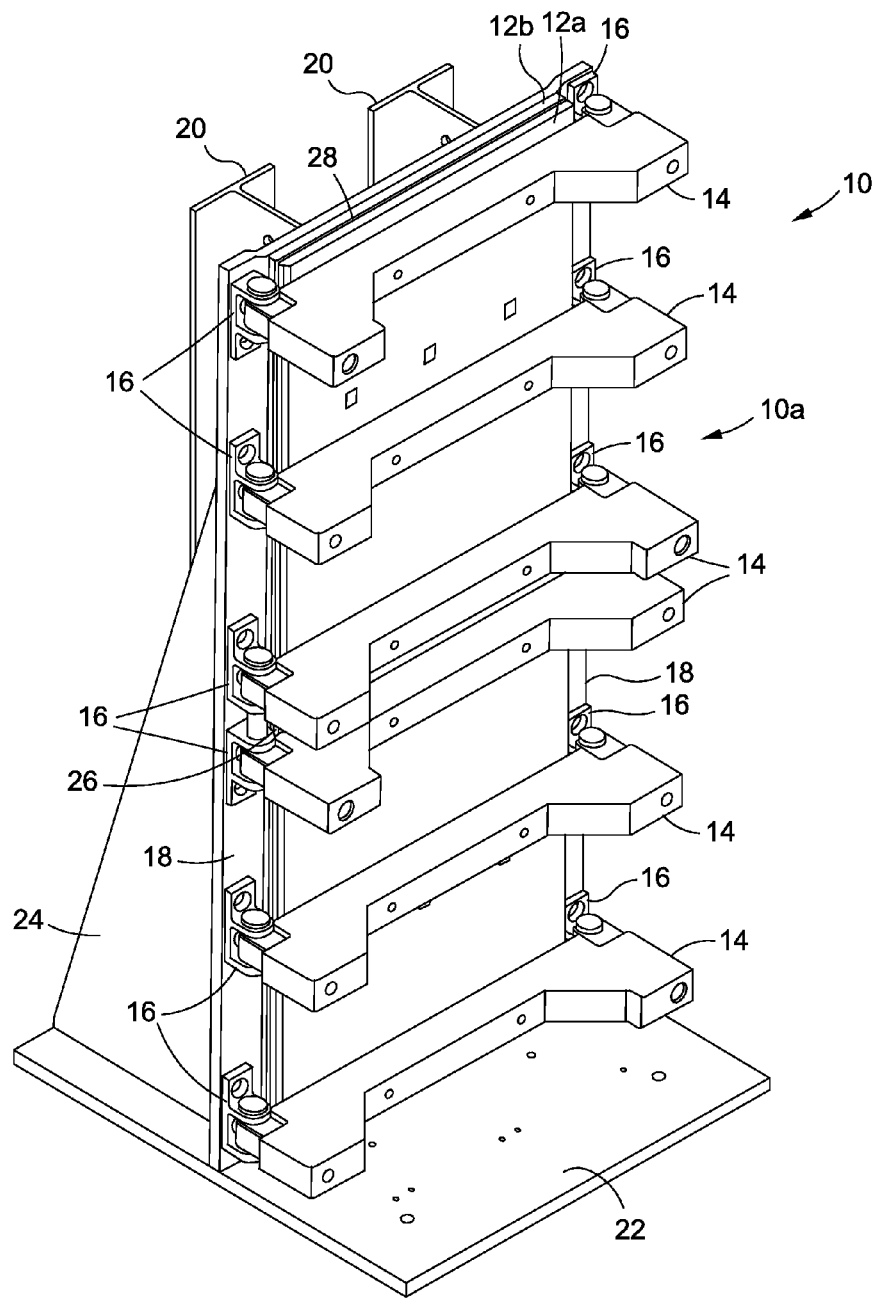
FIG. 1 is an illustration of a front perspective view of an existing test fixture for compression testing.

For example, test specimens 80 (see FIG. 2H), such as in the form of test panels 80*a* (see FIG. 2H), using disclosed embodiments of the apparatus 30 (see FIG. 2A), system 100 (see FIGS. 3A, 5), and method 160 (see FIG. 6), may be tested at a test rate of ten (10) to twenty (20) or more test specimens 80 per day. In contrast, test specimens 28 (see FIG. 1) using an existing test fixture 10 (see FIG. 1), for example, an existing large notch compression test fixture 10*a* (see FIG. 1), may typically be tested at a test rate of only one (1) to two (2) test specimen panels 28 (see FIG. 1) per day.

Further, disclosed embodiments of the apparatus 30 (see FIG. 2A), system 100 (see FIGS. 3A, 5), and method 160 (see FIG. 6), do not require the use and installation of strain gages 14 (see FIG. 1) for testing. This reduces the labor, installation, and flow time required for testing. This, in turn, may result in an overall reduction in the time and expense of testing. Such reduction in the time and expense of testing may preferably be reduced by as much as ten (10) to twenty (20) times, as compared to the time and expense of testing using an existing test fixture 10 (see FIG. 1), for example, existing large notch compression test fixture 10*a* (see FIG. 1).

Moreover, disclosed embodiments of the apparatus 30 (see FIG. 2A), system 100 (see FIGS. 3A, 5), and method 160 (see FIG. 6), may be used with an optical strain measurement system 120 (see FIGS. 3A, 4A), due to the see-through configuration of the support grids 34 (see FIG. 2A) of the apparatus 30 (see FIG. 2A) used for the testing. In contrast, existing test fixture 10 (see FIG. 1), for example, existing large notch compression test fixture 10*a* (see FIG. 1), cannot use the optical strain measurement system 120 (see FIGS. 3A, 4A). This is because the first support plate 12*a* (see FIG. 1) and second support plate 12*b* (see FIG. 1) of the existing large notch compression test fixture 10*a* completely cover and obstruct any view of the test specimen panel 28 (see FIG. 1).

In addition, disclosed embodiments of the apparatus 30 (see FIG. 2A), system 100 (see FIGS. 3A, 5), and method 160 (see FIG. 6), utilize a base platform 62 (see FIG. 2A) that is rigid and crushable, and utilize an end load element 74 (see FIG. 2A) mounted on the base assembly 60 (see FIG. 2A). The end load element 74 (see FIG. 2A) may be replaced after one or more compression tests and is designed to protect the base assembly 60 (see FIG. 2A) during compression testing.

Thus, the base assembly 60 is designed to withstand wear and tear over numerous compression tests, as compared to base structures of certain existing test fixtures. For example, the base portion 22 (see FIG. 1) of existing test fixture 10 (see FIG. 1), such as existing large notch compression test fixture 10*a* (see FIG. 1), may be thin and wear out quickly after several compression tests.

Moreover, disclosed embodiments of the apparatus 30 (see FIG. 2A), system 100 (see FIGS. 3A, 5), and method 160 (see FIG. 6), utilize a base platform 62 (see FIG. 2A) that does not require shimming to reinforce the base platform 62. This may result in reduced time and expense to install the shimming for each test. In contrast, for example, the base portion 22 (see FIG. 1) of an existing test fixture 10, such as existing large notch compression test fixture 10*a* (see FIG. 1), may require the use of shims 20 (see FIG. 1) to reinforce the base portion 22 (see FIG. 1).

Finally, disclosed embodiments of the apparatus 30 (see FIG. 2A), system 100 (see FIGS. 3A, 5), and method 160 (see FIG. 6), utilize one or more load leveling devices 92 (see FIG.

3B) that may be used to self-level or self-balance the load during compression testing of the test specimen 80 (see FIG. 2H).

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. An apparatus for compression testing of a test specimen having a notch portion, the apparatus configured for use with an optical strain measurement system, the apparatus comprising:
    a base assembly having an end load element attached to the base assembly, the base assembly being rigid;
    a support assembly attached to the base assembly, the support assembly having a plurality of window portions; and
    a core assembly installed within the support assembly, the core assembly being crushable and configured to protect the support assembly and the base assembly from fracture loads generated by the test specimen positioned adjacent the core assembly, when the test specimen is fractured or broken during compression testing;
    wherein, when the test specimen is installed in the support assembly, the test specimen and the notch portion are visible to the optical strain measurement system through the plurality of window portions.

2. The apparatus of claim 1 wherein the support assembly comprises a first support grid configured for attachment to a second support grid, the core assembly and the test specimen being installed between the first support grid and the second support grid.

3. The apparatus of claim 2 wherein the first support grid and the second support grid each comprise a frame portion, a plurality of vertical members, and a plurality of horizontal members, the plurality of vertical members and horizontal members forming the plurality of window portions.

4. The apparatus of claim 1 wherein the core assembly comprises a plurality of vertical core elements, each vertical core element comprising a honeycomb sandwich core assembly.

5. The apparatus of claim 1 wherein the core assembly has a crush zone corresponding to a location of the notch portion in the test specimen when the test specimen is installed in the support assembly.

6. The apparatus of claim 1 further comprising a first grip fixture and a second grip fixture, the first grip fixture coupled to the base assembly and configured to hold a first end of the test specimen when the test specimen is installed in the support assembly, and the second grip fixture attached to a second end of the test specimen and configured to apply a pressure load across the second end of the test specimen.

7. The apparatus of claim 1 wherein the end load element comprises an end load wear strip that is removable, replaceable and configured to protect the base assembly during compression testing.

8. A system for compression testing of a test specimen having a notch portion, the system comprising:
    an apparatus comprising:
        a base assembly having an end load element attached to the base assembly, the base assembly being rigid;
        a support assembly attached to the base assembly, the support-assembly having a plurality of window portions; and
        a core assembly installed within the support assembly, the core assembly being crushable and configured to protect the support assembly and the base assembly from fracture loads generated by the test specimen positioned adjacent the core assembly, when the test specimen is fractured or broken during compression testing;
    the test specimen installed in the support assembly of the apparatus;
    a testing machine configured to apply one or more compression loads to the test specimen when the apparatus with the test specimen is installed in the testing machine;
    a testing machine controller coupled to the testing machine and configured to control operation of the testing machine;
    an optical strain measurement system positioned in relation to the apparatus with the test specimen installed in the testing machine, so that the test specimen and the notch portion are visible to the optical strain measurement system through the plurality of window portions; and
    a data acquisition system coupled to the optical strain measurement system.

9. The system of claim 8 further comprising one or more load leveling devices coupled to the apparatus installed in the testing machine.

10. The system of claim 8 wherein the support assembly comprises a first support grid configured for attachment to a second support grid, the first support grid and the second support grid each comprising a frame portion, a plurality of vertical members, and a plurality of horizontal members, the plurality of vertical members and horizontal members forming the plurality of window portions.

11. The system of claim 8 wherein the core assembly has a crush zone corresponding to a location of the notch portion in the test specimen when the test specimen is installed in the support assembly of the apparatus.

12. The system of claim 8 wherein the test specimen comprises a test panel of an aircraft.

13. The system of claim 8 wherein the notch portion of the test specimen is perpendicular to a direction of the one or more compression loads applied by the testing machine to the test specimen.

14. The system of claim 8 wherein the optical strain measurement system comprises two or more optical devices configured to both capture and scan optical measurements at a plurality of locations on the test specimen.

15. The system of claim 8 further comprising a first processing unit coupled to the testing machine controller and a second processing unit of the data acquisition system, the second processing unit coupled to an optical strain measurement system controller of the data acquisition system.

16. A method for compression testing of a test specimen having a notch portion, the method comprising the steps of:
    forming an apparatus for compression testing of a test specimen, the apparatus comprising:
        a base assembly having an end load element attached to the base assembly, the base assembly being rigid;
        a support assembly attached to the base assembly, the support assembly having a plurality of window portions; and
        a core assembly installed within the support assembly, the core assembly being crushable and configured to protect the support assembly and the base assembly from fracture loads generated by the test specimen positioned adjacent the core assembly, when the test specimen is fractured or broken during compression testing;

forming the notch portion in the test specimen;

installing the test specimen within the support assembly and adjacent to the core assembly;

installing the apparatus in a testing machine for compression testing;

positioning an optical strain measurement system in relation to the apparatus, so that the test specimen and the notch portion are visible to the optical strain measurement system through the plurality of window portions;

applying one or more compression loads to the test specimens; and measuring strain data of the test specimen with the optical strain measurement system.

17. The method of claim 16 further comprising after the strain data measuring step, the step of processing the strain data with a data acquisition system.

18. The method of claim 17 further comprising after the step of processing the strain data, the step of replacing the end load element if damaged and replacing any damaged portions of the core assembly.

19. The method of claim 16 wherein the step of installing the apparatus in the testing machine comprises coupling one or more load leveling devices to the apparatus.

20. The method of claim 16 wherein the strain data measuring step comprises using two or more optical devices to capture and scan optical measurements at a plurality of locations on the test specimen.

* * * * *